(12) United States Patent
Lewnard et al.

(10) Patent No.: US 8,110,395 B2
(45) Date of Patent: Feb. 7, 2012

(54) PHOTOBIOREACTOR SYSTEMS AND METHODS FOR TREATING $CO_2$-ENRICHED GAS AND PRODUCING BIOMASS

(75) Inventors: John J. Lewnard, Westford, MA (US); Xiaoxi Wu, Sudbury, MA (US)

(73) Assignee: Algae Systems, LLC, Chicago, IL (US)

( * ) Notice: Subject to any disclaimer, the term of this patent is extended or adjusted under 35 U.S.C. 154(b) by 1379 days.

(21) Appl. No.: 11/818,962

(22) Filed: Jul. 10, 2006

(65) Prior Publication Data
US 2008/0178739 A1  Jul. 31, 2008

(51) Int. Cl.
*C12M 1/00* (2006.01)
(52) U.S. Cl. ............... 435/292.1; 435/293.1; 47/1.4
(58) Field of Classification Search ............ 435/292.1, 435/293.1; 47/1.4
See application file for complete search history.

(56) References Cited

U.S. PATENT DOCUMENTS

| | | | |
|---|---|---|---|
| 1,995,970 A | 3/1935 | Dorough | |
| 2,703,316 A | 3/1955 | Schneider | |
| 2,732,663 A | 1/1956 | Dewey | |
| 2,807,912 A | 10/1957 | Bjorksten | |
| 2,854,792 A * | 10/1958 | Juda | 435/257.3 |
| 3,420,737 A | 1/1969 | Bongers et al. | |
| 3,420,739 A | 1/1969 | Bongers et al. | |
| 3,456,928 A | 7/1969 | Selway | |
| 3,468,057 A | 9/1969 | Buisson et al. | |
| 3,492,789 A | 2/1970 | Jueng | |
| 3,579,907 A * | 5/1971 | Graves | 47/17 |
| 3,592,631 A | 7/1971 | Cattelain | |
| 3,650,068 A | 3/1972 | Meyer et al. | |
| 3,954,615 A | 5/1976 | Shelef | |
| 3,954,921 A | 5/1976 | Yoshida et al. | |
| 3,955,317 A | 5/1976 | Gudin | |
| 3,998,186 A | 12/1976 | Hodges | |
| 4,005,015 A | 1/1977 | Boward, Jr. | |
| 4,044,500 A | 8/1977 | Hitzman | |

(Continued)

FOREIGN PATENT DOCUMENTS

AT    154828 T    7/1997

(Continued)

OTHER PUBLICATIONS

International Search Report and Written Opinion from International Patent Application No. PCT/US2007/015513, dated Feb. 2, 2008.

(Continued)

*Primary Examiner* — William H Beisner
(74) *Attorney, Agent, or Firm* — Peters Verny, LLP

(57) ABSTRACT

Certain embodiments and aspects of the present invention relate to a photobioreactor including covered photobioreactor units through which a liquid medium stream and a gas stream flow. The liquid medium comprises at least one species of phototrophic organism therein. Certain methods of using the photobioreactor system as part of fuel generation system and/or a gas-treatment process or system at least partially remove certain undesirable pollutants from a gas stream. In certain embodiments, a portion of the liquid medium is diverted from a photobioreactor unit and reintroduced upstream of the diversion position. In certain embodiments, the disclosed photobioreactor system, methods of using such systems, and/or gas treatment apparatus and methods provided herein can be used as part of an integrated combustion method and system, wherein photosynthetic organisms used within the photobioreactor are harvested from the photobioreactor, processed, and used as a fuel source for a combustion system such as an electric power plant.

14 Claims, 23 Drawing Sheets

U.S. PATENT DOCUMENTS

| | | | |
|---|---|---|---|
| 4,169,050 A | 9/1979 | Serfling et al. | |
| 4,209,943 A | 7/1980 | Moeller et al. | |
| 4,217,728 A | 8/1980 | Shimamatsu et al. | |
| 4,233,958 A | 11/1980 | Heden | |
| 4,253,271 A | 3/1981 | Raymond | |
| 4,341,038 A | 7/1982 | Bloch et al. | |
| 4,442,211 A | 4/1984 | Greenbaum | |
| 4,446,236 A | 5/1984 | Clyde | |
| 4,473,970 A | 10/1984 | Hills | |
| 4,532,210 A | 7/1985 | Miura et al. | |
| 4,577,110 A | 3/1986 | MacBride | |
| 4,653,223 A | 3/1987 | Mori | |
| 4,658,757 A | 4/1987 | Cook | |
| 4,666,852 A | 5/1987 | Cork | |
| 4,676,956 A | 6/1987 | Mori | |
| 4,786,598 A | 11/1988 | Lafferty et al. | |
| 4,828,768 A | 5/1989 | Talmor | |
| 4,868,123 A | 9/1989 | Berson et al. | |
| 4,888,912 A | 12/1989 | Murray | |
| 4,963,486 A | 10/1990 | Hang | |
| 4,999,302 A | 3/1991 | Kahler et al. | |
| 5,104,589 A | 4/1992 | Palmer et al. | |
| 5,137,828 A | 8/1992 | Robinson et al. | |
| 5,142,023 A | 8/1992 | Gruber et al. | |
| 5,151,347 A | 9/1992 | Delente et al. | |
| 5,162,051 A | 11/1992 | Hoeksema | |
| 5,213,976 A | 5/1993 | Blauhut et al. | |
| 5,216,976 A * | 6/1993 | Marinkovich | 119/200 |
| 5,242,827 A | 9/1993 | Chaumont et al. | |
| 5,247,058 A | 9/1993 | Gruber et al. | |
| 5,247,059 A | 9/1993 | Gruber et al. | |
| 5,250,427 A | 10/1993 | Weaver et al. | |
| 5,258,488 A | 11/1993 | Gruber et al. | |
| 5,269,819 A | 12/1993 | Porath | |
| 5,274,073 A | 12/1993 | Gruber et al. | |
| 5,310,865 A | 5/1994 | Enomoto et al. | |
| 5,330,639 A | 7/1994 | Murphree | |
| 5,338,673 A * | 8/1994 | Thepenier et al. | 435/134 |
| 5,344,557 A | 9/1994 | Scanzillo | |
| 5,357,035 A | 10/1994 | Gruber et al. | |
| 5,359,026 A | 10/1994 | Gruber | |
| 5,424,209 A | 6/1995 | Kearney | |
| 5,440,008 A | 8/1995 | Ichikawa et al. | |
| 5,443,985 A | 8/1995 | Lu et al. | |
| 5,444,143 A | 8/1995 | Ohta et al. | |
| 5,447,629 A | 9/1995 | Chaumont et al. | |
| 5,496,923 A | 3/1996 | Suizu et al. | |
| 5,510,526 A | 4/1996 | Baniel et al. | |
| 5,512,653 A | 4/1996 | Ohta et al. | |
| 5,528,856 A | 6/1996 | Smith et al. | |
| 5,534,417 A | 7/1996 | Arad et al. | |
| 5,541,056 A | 7/1996 | Huntley et al. | |
| 5,554,291 A | 9/1996 | Scanzillo | |
| 5,591,341 A | 1/1997 | Jensen | |
| 5,594,095 A | 1/1997 | Gruber et al. | |
| 5,606,170 A | 2/1997 | Saaski et al. | |
| 5,612,188 A | 3/1997 | Shuler et al. | |
| 5,614,378 A | 3/1997 | Yang et al. | |
| 5,628,311 A | 5/1997 | Mauze | |
| 5,636,472 A | 6/1997 | Spira et al. | |
| 5,659,977 A | 8/1997 | Jensen et al. | |
| 5,661,017 A | 8/1997 | Dunahay et al. | |
| 5,670,046 A | 9/1997 | Kimmel | |
| 5,679,767 A | 10/1997 | Suizu et al. | |
| 5,686,276 A | 11/1997 | Laffend et al. | |
| 5,691,424 A | 11/1997 | Suzuki et al. | |
| 5,714,573 A | 2/1998 | Randall et al. | |
| 5,741,702 A | 4/1998 | Lorenz | |
| 5,766,474 A | 6/1998 | Smith et al. | |
| 5,770,683 A | 6/1998 | Yoshida et al. | |
| 5,780,678 A | 7/1998 | Baniel et al. | |
| 5,786,185 A | 7/1998 | Tsao et al. | |
| 5,798,435 A | 8/1998 | Gruber et al. | |
| 5,846,816 A | 12/1998 | Forth | |
| 5,882,849 A | 3/1999 | Leonard et al. | |
| 5,892,109 A | 4/1999 | Baniel et al. | |
| 5,910,254 A | 6/1999 | Guelcher et al. | |
| 5,917,010 A | 6/1999 | Goto et al. | |
| 5,922,832 A | 7/1999 | Randall et al. | |
| 5,942,597 A | 8/1999 | Noda et al. | |
| 5,958,761 A | 9/1999 | Yogev et al. | |
| 5,981,271 A | 11/1999 | Doucha et al. | |
| 5,998,552 A | 12/1999 | Gruber et al. | |
| 6,005,067 A | 12/1999 | Gruber et al. | |
| 6,022,701 A | 2/2000 | Boussiba et al. | |
| 6,025,184 A | 2/2000 | Laffend et al. | |
| 6,037,170 A | 3/2000 | Sekine | |
| 6,051,437 A | 4/2000 | Luo et al. | |
| 6,083,740 A | 7/2000 | Kodo et al. | |
| 6,087,532 A | 7/2000 | Baniel et al. | |
| 6,111,137 A | 8/2000 | Suizu et al. | |
| 6,140,458 A | 10/2000 | Terado et al. | |
| 6,156,561 A | 12/2000 | Kodo et al. | |
| 6,174,720 B1 | 1/2001 | Oxley et al. | |
| 6,187,951 B1 | 2/2001 | Baniel et al. | |
| 6,218,173 B1 | 4/2001 | Naito | |
| 6,229,046 B1 | 5/2001 | Eyal et al. | |
| 6,277,951 B1 | 8/2001 | Gruber et al. | |
| 6,285,807 B1 | 9/2001 | Walt et al. | |
| 6,291,597 B1 | 9/2001 | Gruber et al. | |
| 6,320,077 B1 | 11/2001 | Eyal et al. | |
| 6,326,458 B1 | 12/2001 | Gruber et al. | |
| 6,348,347 B1 | 2/2002 | Hirabayashi et al. | |
| 6,370,815 B1 | 4/2002 | Skill et al. | |
| 6,416,993 B1 | 7/2002 | Wexler et al. | |
| 6,417,266 B1 | 7/2002 | Terado et al. | |
| 6,428,767 B1 | 8/2002 | Burch et al. | |
| 6,429,280 B1 | 8/2002 | Hiraoka et al. | |
| 6,465,240 B1 | 10/2002 | Wexler et al. | |
| 6,472,559 B2 | 10/2002 | Baniel et al. | |
| 6,475,759 B1 | 11/2002 | Carlson et al. | |
| 6,485,947 B1 | 11/2002 | Rajgarhia et al. | |
| 6,492,149 B1 | 12/2002 | Muller-Feuga | |
| 6,495,631 B1 | 12/2002 | Randall et al. | |
| 6,509,188 B1 | 1/2003 | Trosch et al. | |
| 6,534,679 B2 | 3/2003 | Eyal et al. | |
| 6,575,714 B2 | 6/2003 | Pace et al. | |
| 6,579,714 B1 | 6/2003 | Hirabayashi et al. | |
| 6,602,703 B2 | 8/2003 | Dutil | |
| 6,603,069 B1 | 8/2003 | Muhs et al. | |
| 6,616,845 B2 | 9/2003 | Shechter et al. | |
| 6,648,949 B1 | 11/2003 | Der et al. | |
| 6,667,171 B2 | 12/2003 | Bayless et al. | |
| 6,673,532 B2 | 1/2004 | Rao | |
| 6,706,963 B2 | 3/2004 | Gaudiana et al. | |
| 6,726,838 B2 | 4/2004 | Shechter et al. | |
| 6,827,036 B2 | 12/2004 | Connolly | |
| 7,523,370 B1 | 4/2009 | Keller | |
| 7,755,675 B2 | 7/2010 | Ejima et al. | |
| 2002/0072109 A1 | 6/2002 | Bayless et al. | |
| 2002/0146817 A1 | 10/2002 | Cannon et al. | |
| 2003/0040104 A1 | 2/2003 | Barbera-Guillen | |
| 2003/0056821 A1 | 3/2003 | Chittibaba et al. | |
| 2003/0160500 A1 | 8/2003 | Drake et al. | |
| 2003/0188777 A1 | 10/2003 | Gaudiana | |
| 2003/0189402 A1 | 10/2003 | Gaudiana | |
| 2003/0192583 A1 | 10/2003 | Ryan | |
| 2003/0192584 A1 | 10/2003 | Beckenbaugh | |
| 2003/0192585 A1 | 10/2003 | Beckenbaugh | |
| 2003/0230337 A1 | 12/2003 | Gaudiana | |
| 2004/0025933 A1 | 2/2004 | Chittibabu | |
| 2004/0025934 A1 | 2/2004 | Chittibabu | |
| 2004/0031520 A1 | 2/2004 | Ryan | |
| 2004/0089592 A1 | 5/2004 | Shechter et al. | |
| 2004/0118447 A1 | 6/2004 | Muhs | |
| 2004/0118448 A1 | 6/2004 | Scher | |
| 2004/0207102 A1 | 10/2004 | Sugimori et al. | |
| 2004/0209256 A1 | 10/2004 | Dillon | |
| 2004/0262980 A1 | 12/2004 | Watson | |
| 2005/0014239 A1 | 1/2005 | Melis et al. | |
| 2005/0025367 A1 | 2/2005 | Jodoin | |
| 2005/0064577 A1 | 3/2005 | Berzin | |
| 2005/0239182 A1 | 10/2005 | Berzin | |
| 2005/0260553 A1 * | 11/2005 | Berzin | 435/3 |
| 2006/0016760 A1 | 1/2006 | Bozak et al. | |
| 2006/0048920 A1 | 3/2006 | Helleur | |
| 2007/0048848 A1 | 3/2007 | Sears | |

| | | | |
|---|---|---|---|
| 2007/0048859 A1 * | 3/2007 | Sears | 435/289.1 |
| 2008/0009055 A1 | 1/2008 | Lewnard | |
| 2008/0178739 A1 | 7/2008 | Lewnard | |
| 2009/0011492 A1 | 1/2009 | Berzin | |
| 2009/0130706 A1 | 5/2009 | Berzin et al. | |

FOREIGN PATENT DOCUMENTS

| | | |
|---|---|---|
| AU | 3000084 A | 1/1985 |
| AU | 543516 B2 | 4/1985 |
| AU | 2294788 A | 4/1989 |
| AU | 654114 B2 | 10/1994 |
| AU | 7131696 A | 4/1997 |
| AU | 704463 B2 | 4/1999 |
| AU | 722744 B2 | 8/2000 |
| AU | 2005274791 A1 | 2/2006 |
| AU | 2007273128 A1 | 1/2008 |
| BR | 9007742 A | 11/1992 |
| CA | 1256770 A1 | 7/1989 |
| CA | 2067348 A1 | 11/1991 |
| CA | 2232707 A1 | 3/1997 |
| DE | 282839 A5 | 9/1990 |
| DE | 3888274 T2 | 9/1994 |
| DE | 4411486 C1 | 3/1995 |
| DE | 4420392 A1 | 12/1995 |
| DE | 69030976 T2 | 7/1997 |
| DE | 69030976 T2 | 10/1997 |
| EP | 0130586 A2 | 1/1985 |
| EP | 0310522 A | 4/1989 |
| EP | 0343885 A1 | 11/1989 |
| EP | 0494887 B1 | 6/1997 |
| EP | 0852616 A1 | 7/1998 |
| EP | 2046938 A2 | 4/2009 |
| EP | 2152848 | 2/2010 |
| ES | 434392 A1 | 4/1977 |
| ES | 2103745 T3 | 10/1997 |
| FR | 2324224 A1 | 4/1977 |
| FR | 2596412 A1 | 3/1986 |
| FR | 2596412 A * | 10/1987 |
| FR | 2621323 A1 | 4/1989 |
| GB | 1189096 | 4/1970 |
| GB | 1495709 A | 12/1977 |
| GB | 2118572 A | 11/1983 |
| IL | 87832 A | 3/1992 |
| IT | 1033117 B | 7/1979 |
| IT | 01241751 | 10/1990 |
| JP | 50105881 A | 8/1975 |
| JP | 52028990 A | 3/1977 |
| JP | 58035676 B | 8/1983 |
| JP | 1201436 C | 4/1984 |
| JP | 60012913 A | 1/1985 |
| JP | 1108973 A | 4/1989 |
| JP | 02104231 A | 4/1990 |
| JP | 2058896 B | 12/1990 |
| JP | 1630175 C | 12/1991 |
| JP | 5503418 T | 6/1993 |
| JP | 05184347 A | 7/1993 |
| JP | 05184348 | 7/1993 |
| JP | 5184348 A | 7/1993 |
| JP | 05184348 A | 7/1993 |
| JP | 06350119 A | 12/1994 |
| JP | 2645254 B2 | 8/1997 |
| JP | 11075813 A | 3/1999 |
| JP | 2000504924 T | 4/2000 |
| JP | 3061467 B2 | 7/2000 |
| JP | 2001354407 | 12/2001 |
| NO | 921371 A | 6/1992 |
| NO | 981082 A | 5/1998 |
| TW | 519548 B | 2/2003 |
| WO | WO 91/05849 A1 | 5/1991 |
| WO | WO 9105849 | 5/1991 |
| WO | WO 9105849 A1 | 5/1991 |
| WO | WO 9322418 A1 | 11/1993 |
| WO | WO 9506111 A1 | 3/1995 |
| WO | WO 9603494 A1 | 2/1996 |
| WO | WO 9711154 | 3/1997 |
| WO | WO 9728274 A1 | 8/1997 |
| WO | WO 9800559 A1 | 1/1998 |
| WO | WO 9829531 A1 | 7/1998 |
| WO | WO 0012673 A1 | 3/2000 |
| WO | WO 0104263 A2 * | 1/2001 |
| WO | WO 0104263 A2 | 1/2001 |
| WO | WO 0168257 | 9/2001 |
| WO | WO 0174990 A1 | 10/2001 |
| WO | WO 03015364 | 2/2003 |
| WO | WO 03038348 A1 | 5/2003 |
| WO | WO 03067213 A2 | 8/2003 |
| WO | WO 03094598 | 11/2003 |
| WO | WO 03094598 A1 | 11/2003 |
| WO | WO 2004033075 A1 | 4/2004 |
| WO | WO 2004074423 A2 | 9/2004 |
| WO | WO 2005006838 A2 | 1/2005 |
| WO | WO 2005072254 A2 | 8/2005 |
| WO | WO 2005079650 A1 | 9/2005 |
| WO | WO 2005101525 A3 | 10/2005 |
| WO | WO 2006/002017 A1 | 2/2006 |
| WO | WO 2006020177 | 2/2006 |
| WO | WO 2006020177 A | 2/2006 |
| WO | WO 2007011343 | 1/2007 |
| WO | WO 2007038605 | 4/2007 |
| WO | WO 2008008262 | 1/2008 |
| WO | WO 2008008263 | 1/2008 |
| WO | WO 2008178739 A1 | 7/2008 |
| WO | WO 2008134010 A2 | 11/2008 |
| ZA | 7500373 A | 8/1976 |

OTHER PUBLICATIONS

*Handbook of Microalgal Culture*, Edited by Amos Richmond, "Mass Production of Microalgae: Photobioreactors," Mario R. Tredici, Chapter 9, Blackwell Science Ltd., Oxford, United Kingdom, 2004, pp. 178-214.

U.S. Appl. No. 11/632,541, Isaac Berzin, Photobioreactor Cell Culture Systems, Methods for Preconditioning Photosynthetic Organisms, and Cultures of Photosynthetic Organisms Produced Thereby, filed Mar. 14, 2008.

U.S. Appl. No. 12/110,178, Isaac Berzin, Photobioreactor Systems Positioned on Bodies of Water, filed Apr. 25, 2008.

Antal, Jr., J.J., G. Varhegyi, and E. Jakab (1998) Cellulose Pyrolysis Kinetics: Revisted, Industrial Engineering Chemical Research, vol. 37, pp. 1267-1275.

Antal, Jr., M.J., S.G. Allen, D. Schulman and X. Xu 2000. biomass Gasification in Supercritical Water, Industrial Engineering Chemical Research, vol. 39, pp. 4040-4053.

AU2003234604 Examination Report issued Mar. 27, 2009.

AU2003234604 IDS Submitted Oct. 3, 2007.

AU2007273128 Examination Report, May 2, 2011.

Badawy, W.A., "Imrpoved n-Si/oxide junctions for environmentally safe solar energy conversion," Solar Energy Materials and Solar Cells, Elsevier Science Publishers, Amsterdam, NL, vol. 71, No. 3, Feb. 15, 2002, pp. 281-294.

Benemann, John R., and Oswald, William J., "Systems and Economic Analysis of Microalgae Ponds for Conversion of CO2 to Biomass," Final Report to the Department of Energy Pittsburgh Energy Technology Center under Grant No. DE-FG223-93PC93204, Mar. 21, 1996.

Biohydroge, "Development of Efficient Large-Scale Photogioreactors" James C Ogbonna et al, Chapter 41, "Internal Gas Exchange Photogioreactor" James P Szyper et al, Chaper 53 pp. 329-344 and 441-446, Plenum Press, New York, 1998.

Chao, Kuo-Ping, et al., "Aquacultural characteriscts of *Rhizoclonium riparium* and an evaluation of its biomass growth potential," Journal of Applied Phycology, vol. 17, pp. 67-73, 2005.

Chornet, E., and Czernik S., Renewable Fuels: Harnessing Hydrogen, Nature, vol. 418, pp. 928-929 (2002).

Cortrigh, R. D., R.R. Davda and J.A. Dumesic (2002) "Hydrogen from Catalytic Reforming of Biomass-derived Hydrocarbons in Liquid Water", Nature, vol. 418, 964-967.

Czernik, S., et al., "Hydrogen by Catalytic Steam Reforming of Liquid Byproducts from Biomass Thermoconversion Processes", I&EC Research, vol. 41, pp. 4209-4215 (2002).

Czernik, S., et al., "Hydrogen from Post-Consumer Residues", US DOE Hydrogen, Fuel Cells & Infrastructure Technologies Program—2003 Annual Merit Review Meeting, May 18-22, 2003, Berkeley, CA.

de Luis, J., Vunjak-Novakovic, G., and Searby N.D., Design and Testing of the ISS Cell Culture Unit., Proc. 51st Congress of the Astronautical Federation, rio de Janeiro, Oct. 2-6, 2000.

Dote, Y. et al., "Recovery of liquid fuel from hydrocarbon-rich microalgae by thermochemical liquefaction," Fuel, 1994, 73:12.

Dote, Y., et al., Recovery of liquid fuel from hydrocarbon-rich microalgae by thermochemical liquefaction, Dec. 16, 1993, 3 pages.

Dwi, S., et al., "Utilization of cyanobacterial biomass from water bloom for bioproduction of lactic acid," World Journal of Microbiology & Biotechnology, 17: 259-264, 2001.

Evans, R., et al., "Hydrogen from Biomass: Catalytic Reforming of Pyrolysis Vapors" US DOE Hydrogen, Fuel Cells & Infrastructure Technologies Program—2003 Annual Merit Review Meeting, May 18-22, 2003, Berkeley, CA.

Ginzburg, B., "Liquid Fuel (Oil) From Halophilic Algae: A Renewable Source of Non-Polluting Energy," Renewable Energy, vol. 3, No. 2/3, pp. 249-252, 1993.

Gluz, M.D., et al., Modified Airlift Reactors: The Helical flow Promoters, Chemical Engineering Science, vol. 51, No. 11, pp. 2915-2920, 1996.

Gratzel, M., Molecular Photovoltaics and Mimic Photosynthesis, Pur Appl. Chem, 73:459 (2001).

Gratzel, M., Photoelectrochemical Cells, Nature, 414:338 (2001).

Gray, "Fundamentals of Bitumen Coking Processes Analogous to Granulations: A Critical Review", The Canadian Journal of Chemical Engineering, vol. 80, pp. 393-401, Jun. 2002.

Hamasaki, M., et al., "Influence of CO2, SO2 and NO in flue gas on microalgae productivity," Journal of Chemical Engineering of Japa, 30 (4): 620-624, Aug. 1997, Abstract.

Handbook of Microalgal Culture, Edited by Amost Richmond, "Mass Production of Microalgae: Photobioreactors," Mario R. Tredici, Chapter 9, Blackwell Science, Ltd., Oxford, United Kingdom, 2004, pp. 178-214.

Ike, A., et al., "Hydrogen Photoproduction from CO2-Fixing Microalgal Biomass: Application of Lactic Acid Fermentation by *Lactobacillus amylovorus*," Journal of Fermentaiton and Bioengineering, vol. 84, pp. 428-433 (1997).

Ikuata, Y., et al., "Hydrogen Production by Photosynthetic Microorganisms," In bioHydrogen, Zaborsky et al., eds. Plenum Press, New York, pp. 319-327 (1998).

Intenrational Preliminary Report on Patentability dated Oct. 26, 2006 (PCT/US2005/013108).

International Application No. PCT/US2007/015513 Written Opinion issued Jan. 10, 2009.

International Application PCT/2003/15364 Response to Written Opinion Jun. 1, 2004.

International Application PCT/US2005/025249 IPRP issued Jan. 18, 2008.

International Application PCT/US2005/025367 IPRP issued Jan. 16, 2007.

International Application PCT/US2007/015513 IPRP issued Jan. 13, 2009.

International Patent Application PCT/US2006/37685 Search Report and Written Opinion issued Apr. 2, 2007.

International Preliminary Examination Report PCT/US03/15364 issued Aug. 10, 2004.

International Preliminary Examination Report, PCT/US08/005383, dated Nov. 5, 2009.

International Preliminary Report on Patentability from International Patent Application No. PCT/US2005025249, dated Jan. 31, 2008.

International Preliminary Report on Patentability, PCT/US2008/005383, issued Oct. 27, 2009.

International Search Report (PCT/2003/15364) issued Sep. 3, 2003.

International Search Report and Written Opinion (PCT/US2005/25367) issued Jan. 5, 2006.

International Search Report and Written Opinion from International Patent Application No. PCT/US2007/015514, dated Nov. 23, 2007.

International Search Report and Written Opinion PCT/US2005/013108 issued Jan. 12, 2006.

International Search Report and Written Opinion PCT/US2007/015513, issued Feb. 28, 2008.

International Search Report and Written Opinion, dated Jan. 1, 2006 (PCT/US2005/013108).

International Search Report and Written Opinion, PCT/US2009/040818, issued Jul. 13, 2009.

International Search Report and Written Opinion from International Patent Application No. PCT/US2007/015513, dated Feb. 2, 2008.

International Search Report PCT/US03/15364 issued Sep. 3, 2002.

Kumar, B.S., et al., A γ-ray Tomographic Scanner for Imaging of Void Distribution in Two-Phase Flow Systems, Flow Meas. Instrum., 6(3), 61 (1995).

Kumar, et al., Gas Holdup Measurements in Bubble Columns Using Computed Tomography, AIChE J., 43(6), 1414 (1997).

LaMonica, Martin, "Start-up drills for oil in algae," CNET Press Release, pp. 1-4, May 20, 2005, http://www.news.com.

Larachi, et al., A gamma-ray Detection System for 3D Particle Tracking in Multiphase Reactors, Nucl. Instr. & Meth., A338, 568 (1994).

Laskin, I. and Lechevalier, H.A., Editors, CRC Handbook of Microbiology, Cleveland CRC Press, pp. 519-552 (1977).

Lee, Yuan-Kun, "Enclosed bioreactors for the mass cultivation of photosynthetic microorganisms: the future trend," TIBTECH, Jul. 1986, Elsevier Science Publishers B.V., Amsterdam, pp. 186-189.

Liberman, "Studies of the Chemistry of Hydrocarbons and Their Catalytic Conversions", vol. 30, No. 5, pp. 237-251, (1961).

Magrini-Bair, K. et al., Fluidizable Catalysts for Hydrogen Production from Biomass Pyrolysis/Steam Reforming, US DOE Hydrogen, Fuel Cells & Infrastructure Technologies Program—2003 Annual Merit Review Meeting, May 18-22, 2003, Berkeley, CA.

Maness and Weaver "Hydrogen Production From a Carbon-Monoxide Oxidation Pathway in Rubrivivax gelatinosus", International J. Hydrogen Energy, vol. 27, pp. 1407-1411 (2002).

Merchuk, et al., "Comparison of photobioreactors for cultivation of the red microalga Porphyridium sp," J Chem Technol Biotechnol, 75:1119-1126 (2000).

Merchuk, J., "Why use air-lift bioreactors?", Tibtech, Mar. 1990, vol. 8, pp. 66-71.

Merchuk, J.C., et al., "Light/Dark Cycles in the Growth of the Red Microalga Porphyridium Sp.," Biotechnology and Bioengineering, vol. 59, No. 6, Sep. 20, 1998, pp. 705-713.

Mercury Study Report to Congress, EPA-452/R-97-010, vol. VIII (1997).

Mercury Study Report to congress, EPA-452/R-97-010, vol. VIII, (1997).

Miura, Y. et al., "Stimulation of Hydrogen Production in algal Cells Grown Under High CO2 concentration and Low Temperature," Appliced Biochemistry and Biotechnology, vol. 39/40, pp. 753-761 (1993).

Morita, et al., "Instruciton of microalgal biomass production for practically high photosynthetic perormance using a photobioreactor," Food and Bioproducts Processing, 79 (C3): 176-183 Sep. 2001.

Morita, M., Y. Watanabe and H. Saiki, "Instruction of Microalgal Biomass Production for Practically Higher Photosynthetic Performance Using a Photobioreactor," Trans IchemE., vol. 79, Part C, Sep. 2001.

Nagase, et al., "Improvement of Microalgal NOx Rremoval in Bubble Column and Airlift Reactors," Journal of Fermentation and Bioengineering, vol. 86, No. 4, pp. 421-423, 1998.

Nagase, Hiroyasu, et al., "Characteristics of Biological NOx Removal from Flue Gas in a *Dunaliella tertiolecta* Culture System," Journal of Fermentation and Bioengineering, 83, 1997.

Office Action for Eurasian Application No. 200401492 based on PCT Appl. No. US03/15364 (and claims as pending as of Jun. 2006).

Ogbanna, James C., et al., BioHydrogen, "Development of Efficient Large-Scale Photobioreactors," Chapter 41, "Internal Gas Exchange Photobioreactor," James P. Szyper, et al., Chapter 53, pp. 329-344 and 441-446, Plenum Press, New York, 1998.

O'Regan B., et al., A Low Cost High Efficiency Solar Cell Based on Dye-Sensitized Colloidal TiO2 Films, Nature, 353:737, (1991).

Osburn, L., "Hemp for Fuel" Schaffer Library of Drug Policy, pp. 1-3, printed Nov. 26, 2001, from http://www.druglibrary.org/schaffer/hemp/hempfuel.htm.

Oswald, William J., "The Engineering Aspect of Microalgae," CRC Handbook of Microbiology, Edited by I. Laskin and H.A. Lechevalier, Cleveland CRC Press, 1977, pp. 519-552.

Otsuki, Toshi, et al., "Hydrogen Production by a Floating-Type Photobioreactor," BioHydrogen, Chapter 45, Plenum Press, New York, 1998, pp. 369-374.

Pulz, O., "Photobioreactors: production systems for photorophic microorganisms," Appl Microbiol Biotechnol 57:287-293, Aug. 22, 2001.

Rake, M., "A burning issue," Perspectives, Spring and Summer 1999, pp. 1-7.

Reed T.B. and Gaur S. "Survey of Biomass Gasification" NREL, 2001.

Richmond, Amos, Handbook of Microalgal Culture, Biotechnology and Applied Phycology, Chapter 8 and Ian S.F. Jones, Chapter 33, pp. 125-177 and 534-544, Blackwell Science Ltd., Oxford, United Kingdom, 2004.

Roessler, P. G., et al., "Genetic Engineering Approaches for Enhanced Proudction of Biodiesel Fuel from Microalgae," National Renewable Energy Laboratory, Golden, CO, 1993.

Schlotelburg, C., et al., "Characterization of an Airlift Reactor with Helical Flow Promoters," The Canadian Journal of Chemical Engineering, vol. 77, Oct. 1999, pp. 804-810.

Sheehan, John, Dunhay Terri, Benemann, John R., Roessler Paul, "A Look Back at the U.S. Department of Energy's Aquatic Species Program: Biodiesel from Algae," 1998, NERL/TP-580-24190.

Shimamatsu, H., "Mass production of Spirulina, an edible microalga," Hydrobiologia, 512: pp. 39-44, 2004.

Soule, A., "Greenfuel mixes algae, carbon dioxide to create oil," Mass High Tech, The Journal of New England Technology, Dec. 5, 2001, pp. 1-3.

Sung S., et al., "Biohydrogen Production from Renewable Organic Wastes", US DOE Hydrogen, Fuel Cells & Infrastructure Technologies Program—2003 Annual Merit Review Meeting, May 18-22, 2003, Berkeley CA.

The Algae Alternative, Evan I. Schwartz, The Bostom Globe, Jul. 12, 2004.

Tredici, Mario R., Handbook of Microalgal Culture, Edited by Amos Richmond, Mass Production of Microalgae: Photobioreactors, Chapter 9, Blackwell Science Ltd., Oxford, United Kingdom, 2004, pp. 178-214.

Ugwu, C. U., et al., "Design of static mixers for inclined tubular photobioreactors," Journal of Applied Phycology, vol. 15, pp. 217-223, 2003.

Ugwu, C. U., et al., "Improvement of mass transfer characteristics and productivities of inclined tubular photobioreactors by installationof internal static mixers," Appl Microbiol biotechnol (2002) 58:600-607.

Van Ginkel, S., et al., "Biohydrogen Production as a Function of pH and Substrate Concentration", Environmental Science & Technology, vol. 35, pp. 4726-4730 (2001).

Vunjak-Novakovic, Gordana, et al., "Air-Lift Bioreactors for Algal Growth on Flue Gas: Mathematical Modeling and Pilot-Plant Studies," Ind. Eng. Chem. Res. 2005, vol. 44, pp. 6154-6163.

Vunjak-Novakovic, Gordana, et al., "Microgravity Studies of Cells and Tissues," Ann. N.Y. Acad. Sci. 974:504-517 (2002).

Watanabe, et al., "Photosynthetic CO2 conversion technologies using a photobioreactor incorporation microalgae—Energy and material balances," Energy Conversion and Management, 37 (6-8): 1321-1326 Jun.-Aug. 1996, Abstract.

Wolfrum, E., et al., "Biological Water Gas Shift", US DOE Hydrogen, Fuel Cells & Infrastructure Technologies Program—2003 Annual Merit Review Meeting, 18-22, 2003, Berkeley, CA.

Written Opinion, PCT/US08/005383, dated Apr. 9, 2009.

Wu, Xiaoxi and Merchuk, Jose, C., "A model integrating fluid dynamics in photosynthesis and photoinhibition processes," Chemical Engineering Science, 2001, 56, pp. 3527-3538.

Wu, Xiaoxi, et al., "Stimulation of Algae Growth in a Bench-Scale Bubble column Reactor," Biotechnology and Bioengineering, vol. 80, No. 2, 156-168, Oct. 20, 2002.

Xiaoxi Wu, et al., Measurement of fluid flow in the downcomer of an internal loop airlift reactor using an optical trajectory-tracking system, Chemical Engineering Science 58 (2003) 1599-1614.

Xiaoxi, Wu, et al., "Simulation of Algae growth in a bench scale internal loop airlift reactor," Chemical Engineering Science 59 (2004) 2899-2912.

Yuan-Kun Lee, "Enclosed Bioreactors for the mass cultivation of photosynthetic microorganisms: the future trend," TIBTECH, Jul. 1986, Elsevier Science Publishers B.V., Amsterdam, pp. 186-189.

Zimmerman, J., "Algae emissions reduction concept shows new promise,", Electric Light & Power/Utility Automation and Engineering T&D News, printed Apr. 19, 2005, pp. 1-3.

* cited by examiner

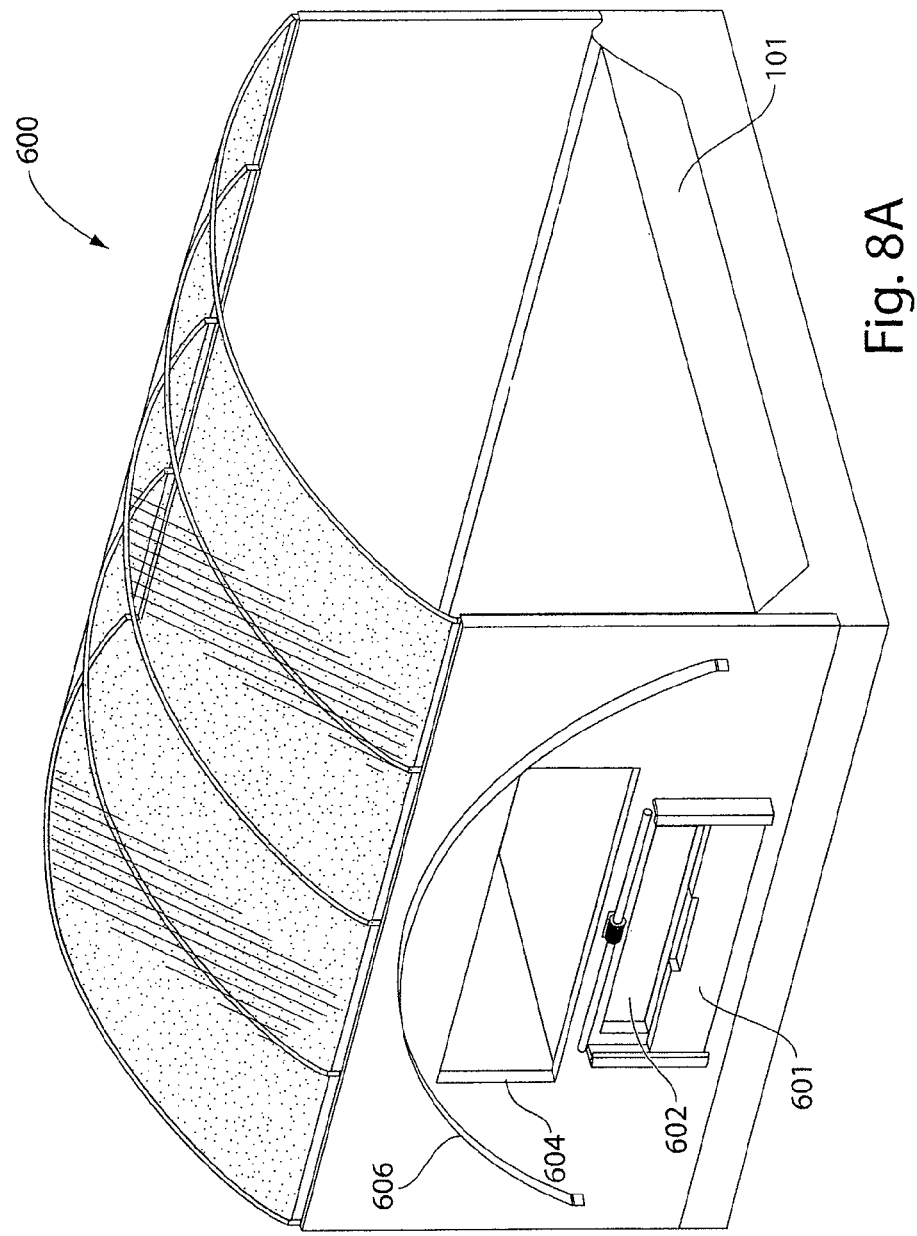

US 8,110,395 B2

PHOTOBIOREACTOR SYSTEMS AND METHODS FOR TREATING $CO_2$-ENRICHED GAS AND PRODUCING BIOMASS

FIELD OF THE INVENTION

The invention relates generally to photobioreactors and processes to operate and use photobioreactors for the treatment of gases, such as flue gases, and for the production of biomass.

DISCUSSION OF THE RELATED ART

The power generation industry is coming under increasing pressure to produce electricity from renewable energy sources. Many biofuels meet renewable energy source standards, however, sources of conventional biofuels, such as biomass, biodiesel, and bioethanol, are not uniformly geographically distributed across the nation, and in general, these sources are not located close to power generation facilities.

At the same time, reductions in carbon dioxide emissions and other gas emissions from various sources are becoming increasingly necessary and/or desirable. Typically, capturing carbon dioxide from the flue gas of anthropogenic sources such as electric power plants is expensive.

Photosynthesis is the carbon recycling mechanism of the biosphere. In this process organisms performing photosynthesis, such as plants, synthesize carbohydrates and other cellular materials by $CO_2$ fixation. One of the most efficient converters of $CO_2$ and solar energy to biomass are microalgae, often referred to herein simply as "algae," which are the fastest growing photoautotrophic organisms on earth and one of nature's simplest microorganisms. In fact, over 90% of $CO_2$ fed to algae can be absorbed, mostly through the production of cell mass. (Sheehan, John; Dunahay, Terri; Benemann, John R.; Roessler, Paul, "A Look Back at the U.S. Department of Energy's Aquatic Species Program: Biodiesel from Algae," 1998, NERL/TP-580-24190; hereinafter "Sheehan et al. 1998"). In addition, algae are capable of growing in saline waters that are unsuitable for agriculture.

Using algal biotechnology, $CO_2$ bio-regeneration can be advantageous due to the production of useful, high-value products from waste $CO_2$. Production of algal biomass as a method of reducing $CO_2$ levels in combustion gas is an attractive concept because dry algae has a heating value roughly equivalent to coal. Algal biomass can also be turned into a high quality liquid fuel which is similar to crude oil or diesel fuel ("biodiesel") through thermochemical conversion by known technologies. Algal biomass also can be used for gasification to produce highly flammable organic fuel gases suitable for use in gas-burning power plants. (e.g., see Reed, T. B. and Gaur, S. "A Survey of Biomass Gasification" NREL, 2001; hereinafter "Reed and Gaur 2001").

Algal cultures also can be used for biological $NO_x$ removal from combustion gases. (Nagase Hiroyasu, Ken-Ichi Yoshihara, Kaoru Eguchi, Yoshiko Yokota, Rie Matsui, Kazumasa Hirata and Kazuhisa Miyamoto, "Characteristics of Biological $NO_x$ Removal from Flue Gas in a *Dunaliella tertiolecta* Culture System," Journal of Fermentation and Bioengineering, 83, 1997; hereinafter "Hiroyasu et al. 1997"). Some algae species can remove $NO_x$ at a wide range of $NO_x$ concentrations and combustion gas flow rates. Nitrous oxide (NO), a major $NO_x$ component, is dissolved in the aqueous phase, after which it is oxidized to $NO_2$ and assimilated by the algal cell. For example, $NO_x$ removal using the algae *Dunaliella* can occur under both light and dark conditions, with an efficiency of $NO_x$ removal of over 96% (under light conditions).

Over an 18-year period, the U.S. Department of Energy (DOE) funded an extensive series of studies to develop renewable transportation fuels from algae (Sheehan et al. 1998). In Japan, government organizations (MITI), in conjunction with private companies, have invested over $250 million into algal biotechnology. Each program took a different approach, but because of various problems addressed by certain embodiments of the present invention, none has been commercially successful to date.

A major obstacle for feasible algal bio-regeneration and pollution abatement has been an efficient, yet cost-effective, growth system. DOE's research focused on growing algae in massive open ponds as big as 4 km². The ponds require low capital input; however, algae grown in open and uncontrolled environments result in low algal productivity. The open pond technology made growing and harvesting the algae prohibitively expensive, because massive amounts of dilute algal waters required very large agitators, pumps and centrifuges. Furthermore, with low algal productivity and large flatland requirements, this approach could, in the best-case scenario, be applicable to only 1% of U.S. power plants. (Sheehan et al. 1998). On the other hand, the MITI approach, with stricter land constraints, focused on very expensive closed algal photobioreactors utilizing fiber optics for light transmission. In these controlled environments, much higher algal productivity was achieved, but the algal growth rates were not high enough to offset the capital costs of the systems utilized. Other examples of closed photobioreactors known in the art include U.S. Pat. Nos. 2,732,663; 4,473,970; 4,233,958; 4,868,123; and 6,827,036.

Burlew (Burlew, John S. "Algal Culture: From Laboratory to Pilot Plant." Carnegie Institution of Washington Publication 600. Washington, D.C., 1961 (hereinafter "Burlew 1961")) provides an overview of several designs for algae bioreactors. The bioreactors discussed in Burlew 1961 include the use of glass tubes, open tanks, open trenches, and covered trenches. In these systems, carbon dioxide is fed into a liquid via gas sparging. More recently, Pulz and Scheibenbogen (Pulz O. and Scheibenbogen K. "Photobioreactors: Design and Performance with Respect to Light Energy Input," *Advances in Biochemical Engineering/Biotechnology*, 59:pp 124-151 (1998); hereinafter "Pulz 1998") reviewed algae photobioreactors, and Richmond (Richmond A. ed. "Handbook of Microalgal Culture—Biotechnology and Applied Phycology, Blackwell Publishing, Oxford, UK (2004); hereinafter "Richmond 2004") reviewed the general state of the art of microalgae culturing, including reactor design. Both references (Richmond 2004 and Pulz 1998) note that open systems, such as natural lakes, circular ponds, and raceway reactors are the predominate commercial technology. Open air systems used for cultivation of algae are also shown in, for example, U.S. Pat. Nos. 3,650,068; 3,468,057; and 4,217,728.

SUMMARY

Certain embodiments and aspects of the present invention relate to: photobioreactor apparatus; gas-treatment systems and methods employing photobioreactors; modular components and systems for photobioreactors; methods and systems for controlling and operating photobioreactors and photobioreactor systems; and integrated combustion/gas-treatment/carbon fuel recycling methods and systems.

According to one aspect of the invention, a photobioreactor is provided in which a gas containing elevated concentrations of carbon dioxide is contacted with a liquid medium containing a phototrophic biological species such as algae. The gas and liquid are contained within an elongated photobioreactor unit having a light-transparent cover, and the biological species uses the carbon dioxide and the light to grow, thereby producing biomass.

The elongated photobioreactor unit may be formed with one or more individual photobioreactor sections which, in the case of more than one section, are interconnected with each other, each section having its own inlet, outlet and associated cover or portion of an integral cover spanning multiple sections. One or more of the photobioreactor units operating in parallel may form a photobioreactor system. However, some embodiments of photobioreactor systems may include a single photobioreactor unit (formed of multiple photobioreactor sections) or even a single photobioreactor section.

According to another aspect of the invention, a modular section-based construction is used in constructing photobioreactor units such that a system may be easily scaled depending on the needs of a particular application. A section-based construction also may permit interchanging of sections having different functions if operating conditions change or if adjustments to the system are desired. In certain embodiments, each unit comprises one photobioreactor section, and a plurality of such sections are arranged in parallel to form a photobioreactor system. In other embodiments, one or more photobioreactor units of a photobioreactor system may be formed from a plurality of photobioreactor sections interconnected together in series.

According to another aspect of the invention, phototrophic organisms, such as algae, and the liquid medium in which they are contained, are diverted from a photobioreactor unit and returned to the same or different photobioreactor unit (or other portion of the system) upstream of the diversion location.

According to another aspect of the invention one or more photobioreactor sections include at least one self-supporting cover which is able to withstand internal/external pressure differences and weather elements.

According to another aspect of the invention, multiple zones within the photobioreactor system are longitudinally (i.e. in the direction of overall media flow) delineated and controlled to provide different operating conditions among the zones.

According to another aspect of the invention, components of a photobioreactor system, such as photobioreactor units and/or photobioreactor sections, are supported by floats on a pond or other body of water.

According to another aspect of the invention, liquid from one or more of various stages of a photobioreactor system is used to quench incoming flue gas.

According to another aspect of the invention, wastewater from a power plant is used to heat photobioreactors.

According to another aspect of the invention, photobioreactors include cooling zones which take advantage of evaporative cooling.

According to another aspect of the invention, a gas stream experiences a low pressure drop while passing through a photobioreactor.

According to another aspect of the invention, photobioreactors are used over large areas which include elevation variations.

According to another aspect of the invention, a photobioreactor system combines the advantages of a plug flow system and a back-mixing system.

According to one embodiment of the invention, a photobioreactor system comprises a plurality of interconnectable photobioreactor sections which, when connected together, form at least one longitudinally-oriented photobioreactor unit of the photobioreactor system, the photobioreactor sections each comprising a liquid flow channel and a light-transparent cover that forms a gas headspace between the cover and the liquid flow channel. The cover is constructed and arranged to cover at least a substantial portion of the liquid flow channel and is configured to be capable of providing the gas headspace even when a gas pressure within the photobioreactor unit is less than the atmospheric pressure surrounding the photobioreactor section.

According to another embodiment of the invention, a photobioreactor system capable of supporting the growth of phototrophic organisms using a gas containing elevated levels of carbon dioxide comprises at least one photobioreactor section constructed and arranged to carry a flow of liquid medium comprising phototrophic organisms therein. The photobioreactor section comprises a cover constructed and arranged to cover at least a substantial portion of the liquid medium within the photobioreactor section and further constructed and arranged to provide a gas headspace under the cover and above the liquid medium, the cover being capable of providing the gas headspace even when a gas pressure within the photobioreactor is less than the atmospheric pressure surrounding the photobioreactor section. The photobioreactor system also comprises a liquid inlet to provide liquid medium to the photobioreactor section, a liquid outlet from which to remove liquid medium comprising phototrophic organisms therein from the photobioreactor section, a gas inlet to provide gas containing an elevated concentration of carbon dioxide into the gas headspace, a gas outlet from which to remove gas containing carbon dioxide at a concentration less than at the gas inlet, and a blower fluidically connected to the gas outlet able to create a flow of gas through the gas headspace from the gas inlet to the gas outlet.

According to a further embodiment of the invention, a photobioreactor system comprises at least one longitudinally extending photobioreactor unit comprising at least one photobioreactor section, the photobioreactor unit being constructed and arranged to carry a flow of liquid medium comprising phototrophic organisms therein. The photobioreactor unit comprises at least one cover constructed and arranged to cover at least a substantial portion of the liquid medium within the photobioreactor unit and constructed and arranged to provide a gas headspace under the cover and above the liquid medium, the cover being capable of providing the gas headspace even when a gas pressure within the gas headspace of the photobioreactor is less than the atmospheric pressure surrounding the photobioreactor unit. The photobioreactor unit further comprises a first liquid inlet constructed and arranged to provide a liquid medium to the photobioreactor unit, a first liquid outlet from which the liquid medium is removable from the photobioreactor unit, a second liquid outlet positioned between the first liquid inlet and the first liquid outlet, from which the liquid medium is removable from the photobioreactor unit, and a channel fluidically interconnecting the second liquid outlet to the photobioreactor unit at a position which is upstream of the second liquid outlet to enable return and recycle of the liquid medium within the photobioreactor unit.

According to another embodiment of the invention, a method of growing phototrophic organisms in a photobioreactor system comprises providing liquid medium comprising phototrophic organisms therein to a first liquid inlet of a longitudinally extending photobioreactor unit, comprising at least one photobioreactor section, such that the liquid medium flows toward a first liquid outlet, the photobioreactor unit having at least one rigidly supported cover. The method further comprises flowing a gas containing an elevated concentration of carbon dioxide over the liquid medium, removing a portion of the liquid medium from the photobioreactor unit at a removal position located between the first liquid inlet and the first liquid outlet, and returning at least some of the removed portion of liquid medium to the photobioreactor unit at a position upstream of the removal position.

According to a further embodiment of the invention, a photobioreactor system capable of supporting the growth of phototrophic organisms using a gas containing an elevated concentration of carbon dioxide comprises at least one photobioreactor section constructed and arranged to carry a flow of liquid medium comprising phototrophic organisms therein. The photobioreactor section comprises a cover constructed and arranged to cover at least a substantial portion of the liquid medium within the photobioreactor section and constructed and arranged to provide a gas headspace under the cover and above the liquid medium, the gas headspace being maintainable at a pressure that differs from atmospheric pressure. The photobioreactor section further comprises a liquid inlet configured to provide liquid medium to the photobioreactor section, a liquid outlet from which liquid medium is removable from the photobioreactor section, and a gas outlet from which gas containing carbon dioxide at a concentration less than at the gas inlet is removable from the photobioreactor section. The photobioreactor section comprises a first portion of the photobioreactor section in which the cover provides the gas headspace over a first portion of the liquid medium, and further comprises a second, different portion of the photobioreactor section in which a second portion of the liquid medium is exposed to gas outside of the gas headspace to facilitate evaporative cooling of the liquid medium.

According to another embodiment of the invention, a photobioreactor system capable of supporting the growth of phototrophic organisms using a gas containing an elevated concentration of carbon dioxide comprises at least one photobioreactor section constructed and arranged to carry a flow of liquid medium comprising phototrophic organisms therein and a flow of gas containing an elevated concentration of carbon dioxide. The photobioreactor system comprises a liquid inlet constructed and arranged to provide at least liquid medium to the photobioreactor section, a liquid outlet from which liquid medium is removable from the photobioreactor section, a gas inlet constructed and arranged to provide gas containing an elevated concentration of carbon dioxide to the photobioreactor section, a gas outlet from which gas containing carbon dioxide at a concentration less than at the gas inlet is removable from the photobioreactor section, and a cover constructed and arranged to cover at least a substantial portion of the flow of liquid medium within the photobioreactor section and constructed and arranged to provide a gas headspace under the cover and above the liquid medium. The photobioreactor section includes a portion of the photobioreactor section where the liquid medium is exposed to gas outside of the gas headspace to facilitate evaporative cooling of the liquid medium. The photobioreactor system also comprises a controller configured to control the amount of evaporative cooling of the liquid medium in the portion of the photobioreactor section where the liquid medium is exposed to gas outside of the gas headspace.

According to yet another embodiment of the invention, a method of removing carbon dioxide from an effluent gas stream containing elevated concentrations of carbon dioxide comprises directing the effluent gas stream through a quench zone, quenching the effluent gas stream in the quench zone using a quench liquid, and directing the quenched effluent gas stream to a photobioreactor system, the effluent gas stream being contacted with liquid medium comprising phototrophic organisms suspended therein such that the phototrophic organisms use carbon dioxide from the effluent gas stream for photosynthesis. The method further comprises removing at least a portion of the liquid medium comprising phototrophic organisms suspended therein from the photobioreactor system, directing the liquid medium to a dewatering system, dewatering the suspension of phototrophic organisms to produce dewatered biomass and the quench liquid, and directing quench liquid to the quench zone.

According to another embodiment of the invention, a method of removing carbon dioxide from an effluent gas stream containing an elevated concentration of carbon dioxide comprises directing the effluent gas stream through a quench zone, removing liquid medium comprising phototrophic organisms therein from a photobioreactor system, quenching the effluent gas stream in the quench zone using the liquid medium removed from the photobioreactor system, and directing the quenched gas to a photobioreactor system, the quenched gas being contacted with liquid medium comprising phototrophic organisms therein such that the phototrophic organisms use carbon dioxide from the gas for photosynthesis.

BRIEF DESCRIPTION OF THE DRAWINGS

Other advantages, novel features, and uses of the invention will become more apparent from the following detailed description of non-limiting embodiments of the invention when considered in conjunction with the accompanying drawings, which are schematic and which are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention.

In the drawings:

FIG. 6b is a perspective view of a second configuration of the photobioreactor unit zone shown in FIG. 6a;

FIG. 8a is a perspective view of one component of a bulkhead distribution unit according to one embodiment of the invention;

FIG. 8b is a cross-sectional view of the bulkhead distribution unit component shown in FIG. 8a;

DETAILED DESCRIPTION

Figure 1A:
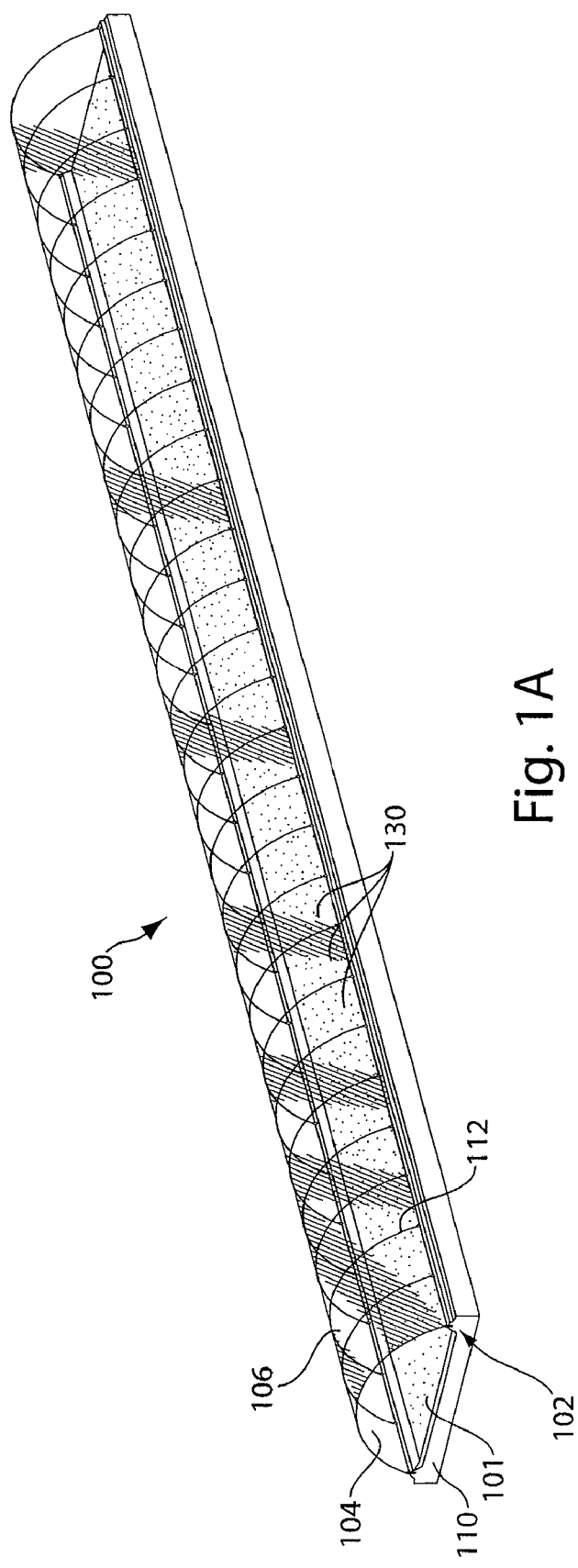
FIG. 1a is a perspective view of a photobioreactor unit according to one embodiment of the invention.

Certain embodiments and aspects of the present invention relate to photobioreactor systems designed to contain a liquid medium comprising at least one species of phototrophic organism therein, and to methods of using the photobioreactor systems as part of a gas-treatment process and system able to at least partially remove certain undesirable pollutants from a gas stream.

Certain embodiments of the invention include one or more longitudinally oriented, elongated covered photobioreactor units arranged in parallel that extend across a land area or a body of water, such as a pond, to form at least a part of a photobioreactor system. In certain embodiments, each photobioreactor unit has a liquid channel (formed by a trench in some embodiments) and a gas headspace (enclosed by a light-transparent cover in some embodiments). $CO_2$-rich gas enters the photobioreactor unit and flows in the headspace above a liquid medium comprising at least one phototrophic organism such as algae. The algae uses the $CO_2$ from the gas and the light that passes through the cover to grow and produce biomass. Algae may be harvested from the liquid medium discharge and dewatered. The dewatered algae may go through additional processes and may be used as fuel and/or used to produce a fuel product (e.g. biodiesel). The liquid produced during the dewatering phase may be recycled back into the same photobioreactor unit and/or a different photobioreactor unit of the photobioreactor system and/or another component of the photobioreactor system in some embodiments. In some cases, the photobioreactor units may be on the order of a few hundred feet or less, while in other cases, the photobioreactor units may extend half a mile or more.

A modular, sectional construction may be used to form at least some portion of at least some of the photobioreactor units in certain embodiments. For example, in certain embodiments, a photobioreactor unit may be made up of a plurality of individual photobioreactor sections interconnected in series. In certain such embodiments, the individual sections may comprise both a liquid flow channel and at least one cover. In other embodiments, a photobioreactor unit may comprise a single, uninterrupted liquid flow channel contained in a base (e.g. base 110 of FIG. 1a), and the photobioreactor sections may be defined by the zones covered by one or a subset of a plurality of cover sections (e.g. see cover sections 106 of FIG. 1a) over the base and channel. In this manner, the length of one or more photobioreactor units may be produced by selecting and interconnecting the appropriate number of photobioreactor sections, and thus custom manufacturing for specific applications may not be required. By employing a modular construction, in some cases, the length may be adjusted after installation if desired. Additionally, various types of photobioreactor sections may be used within a photobioreactor unit to create a plurality of operation zones with selected functionality, such as nutrient misting zones, cooling zones, liquid diversion zones, etc., and the number and positions of the various types of photobioreactor sections may be designed based on predicted operating conditions. Exchanging different types of photobioreactor sections after installation also may be possible when using a modular sectional construction. In some embodiments, a large number of photobioreactor units may be positioned near to one another (e.g. parallel to one another), and system scaling may be achieved by adding or subtracting photobioreactor units.

In certain embodiments, the disclosed photobioreactor systems, methods of using such systems, and/or gas treatment systems and methods provided herein can be used as part of an integrated method and system for treating waste gasses produced by industrial processes, wherein phototrophic organisms used within the photobioreactor at least partially remove certain pollutant compounds contained within effluent gases, e.g. $CO_2$ and/or $NO_x$, and are subsequently harvested from the photobioreactor system, processed, and used as a fuel source for a combustion device (e.g. an electric power plant generator, industrial furnace, and/or incinerator). Such uses of certain embodiments of the invention can provide an efficient means for recycling carbon contained within a combustion fuel (i.e. by converting $CO_2$ in a combustion gas to biomass fuel and/or biomass-derived fuel in a photobioreactor system), thereby reducing both $CO_2$ emissions and fossil fuel requirements.

In some embodiments, the liquid within a photobioreactor unit is sprayed into the gas headspace or otherwise exposed to $CO_2$-rich gas using one or more mass transfer enhancement devices to increase the surface-to-volume ratio of the liquid. By providing surface area contact between the gas and the liquid medium via movement of the gas through a headspace rather than by exclusively sparging gas into a depth of liquid medium, certain embodiments of the photobioreactor system exhibit a low pressure drop when moving gas through the photobioreactor units. In some embodiments, the gas pressure drop along an entire photobioreactor unit may be below 0.5 psi.

In some embodiments, the flow of gas and liquid through the photobioreactor units may experience limited or essentially no backflow, and in this way exhibit the characteristics of a plug flow system. With limited backflow, longitudinal zones may be defined in which different operating conditions such as, for example, algae density, liquid temperature, gas composition, gas temperature, media composition, media agitation/turbulence, gas/liquid mass/heat transfer, light exposure, media depth, etc. are generally known and controllable by changing operating parameters. For example, a single photobioreactor unit may include different zones within which one or more of the following operating parameters vary and/or are known and/or are controllable: nutrient concentrations; temperature; pH; liquid depth; surface-to-air ratio of the liquid; agitation levels; and others. In certain embodiments, these zones may be made up by or comprise one or more specially configured photobioreactor sections of the photobioreactor unit.

In some embodiments, advantages of a back-mixed bioreactor may be achieved while maintaining many of the characteristics of a plug flow bioreactor. One or more reflow zones may be used to return algae-rich liquid from, for example, a longitudinal mid-area of the photobioreactor unit to the front end of the photobioreactor unit or to some other position upstream of the liquid removal position. By doing so, the addition of new innocula to the liquid medium at the front end of the photobioreactor unit may be reduced or eliminated and/or other desirable operating parameters may be maintained and/or established.

Compared to raceway reactors, which can experience considerable thermal loss when ambient temperatures are below the reactor operating temperature, some embodiments of the invention limit thermal loss by covering a majority (or in some cases substantially all) of the liquid surfaces within the photobioreactor system. Compared to typical enclosed photobioreactors (e.g. certain tubular photobioreactors) which do not include a gas head space in contact with the liquid media over at least a substantial portion of its flow length, some of which use various methods of thermal management to remove heat from the reactors, certain embodiments disclosed herein are able to shed heat efficiently using controlled evaporative cooling.

According to certain embodiments, unlike systems that use gas pressure to support a cover, a self-supporting cover(s), e.g. rigid individual interconnected cover section(s) or a continuous or sectioned cover formed of a flexible, non self-supporting material that comprises ribs or other support elements, may be used to maintain a gas headspace regardless of the pressure of the gas flowing through a photobioreactor unit. The cover may be configured such that when gas is pulled through a photobioreactor unit by an induced-draft fan, thereby creating a negative pressure within the photobioreactor unit relative to atmospheric pressure, the cover maintains the gas headspace (i.e. does not collapse). In some embodiments, the cover is constructed and arranged to withstand external forces such as wind and snow.

Certain aspects of the invention are directed to photobioreactor designs and to methods and systems utilizing photobioreactors. A "photobioreactor," "photobioreactor unit" or "photobioreactor section" as used herein, refers to an apparatus containing, or configured to contain, a liquid medium comprising at least one species of phototrophic organism and having either a source of light capable of driving photosynthesis associated therewith, or having at least one surface at least a portion of which is partially transparent to light of a wavelength capable of driving photosynthesis (i.e. light of a wavelength between about 400-700 nm).

The term "photosynthetic organism", "phototrophic organism", or "biomass," as used herein, includes all organisms capable of photosynthetic growth, such as plant cells and micro-organisms (including algae, euglena and lemna) in unicellular or multi-cellular form that are capable of growth in a liquid phase (except that the term "biomass," when appearing in the titles of documents referred to herein or in such references that are incorporated by reference, may be used to more generically to refer to a wider variety of plant and/or animal-derived organic matter). These terms may also include organisms modified artificially or by gene manipulation. While certain photobioreactors disclosed in the context of the present invention are particularly suited for the cultivation of algae, or photosynthetic bacteria, and while in the discussion below, the features and capabilities of certain embodiments that the inventions are discussed in the context of the utilization of algae as the photosynthetic organisms, it should be understood that, in other embodiments, other photosynthetic organisms may be utilized in place of or in addition to algae. For an embodiment utilizing one or more species of algae, algae of various types, (for example *Chlorella, Chlamdomonas, Chaetoceros, Spirolina, Dunaliella, Porphyridum*, etc) may be cultivated, alone or in various combinations, in the photobioreactor.

The phrases "at least partially transparent to light" and "configured to transmit light," when used in the context of certain surfaces or components of a photobioreactor, refers to such surface or component being able to allow enough light energy to pass through, for at least some levels of incident light energy exposure, to drive photosynthesis within a phototrophic organism.

One embodiment of a photobioreactor unit 100 is illustrated in FIGS. 1a and b. Liquid medium 101 flows along a trench (or, equivalently, channel) 102 within photobioreactor unit 100, and gas, such as flue gas from a power plant, flows through a gas headspace 104 formed between liquid medium 101 and a cover(s) 106 at least partially transparent to light. Cover(s) 106 may be constructed such that gas headspace 104 remains essentially constant when no gas pressure or a negative gas pressure is applied to the interior of photobioreactor unit 100.

As $CO_2$-rich gas flows over liquid medium 101, $CO_2$ dissolves into the liquid medium, and algae within the liquid medium use the $CO_2$ and sunlight (or other light source) to photosynthesize, grow and reproduce, thereby producing biomass. The liquid medium flows, in certain embodiments at a controlled rate, through photobioreactor unit 100, and the algae, in certain embodiments, is harvested at an outlet of photobioreactor unit 100 by removing the algae-rich liquid from the photobioreactor unit.

In some embodiments, photobioreactor unit 100 may be approximately 10 meters wide and the overall photobioreactor unit 100 may be a suitable length to process a desired amount of $CO_2$. In general, the photobioreactor unit length exceed the width, and the ratio of length to width may be greater than 100:1, and may exceed 1000:1. The gas containing elevated concentrations of $CO_2$ (i.e., $CO_2$ concentrations which are higher than ambient air) may range from 1%-100%, but typically in the range of 4-20%. The operating pressure of the reactor may generally range from about 11-20 psia, preferably from 13-16 psia. Flow rates of the gas may generally range from about 0.05-50 cm/sec, or other suitable flow rate. Liquid flow rates may generally range from about 1-100 cm/sec. Biomass concentrations generally may range from 0.01-10 g/l.

Several structural features of one embodiment of photobioreactor unit 100 will now be described, but it is important to note that the particular structural implementation of this embodiment are not intended to be limiting.

Base 110 of photobioreactor unit 100 is formed of a compacted gravel base, and cover(s) 106 is supported by structural ribs 112. Structural ribs 112 are attached to supports 114 embedded in trench sidewalls 116 formed of the same material as the base (e.g., compacted gravel). A bottom liner 120 is laid over or formed within the base 110 to provide a liquid impermeable surface. Liner 120 may be, for example a plastic sheet, e.g. a polyethylene sheet, or any other suitable liner.

Cover(s) 106 may be constructed from a wide variety of transparent or translucent materials that are suitable for use in constructing a bioreactor. Some examples include, but are not limited to, a variety of transparent or translucent polymeric materials, such as polyethylenes, polypropylenes, polyethylene terephthalates, polyacrylates, polyvinylchlorides, polystyrenes, polycarbonates, etc. Alternatively, cover(s) 106 may be formed from glass or resin-supported fiberglass. In certain embodiments, cover(s) 106, in certain embodiments in combination with support elements such as support elements 112/114, is sufficiently rigid to be self-supporting and to withstand typical expected forces experienced during operation without collapse or substantial deformation. Portions of cover(s) 106 may be non-transparent in certain embodiments, and such portions can be made out of similar materials as described above for the at least partially transparent portions of cover(s) 106, except that, when they are desired to be non-transparent, such materials should be opaque or coated with a light-blocking material.

Cover(s) 106 may include a material which is UV stabilized and may, in certain embodiments be between about 4-6 mils in thickness, depending on the material. The material, in certain embodiments in combination with support elements such as support elements 112/114, may be designed to support external loads such as snow, wind and/or negatives pressures applied by an induced-draft fan. Additionally, in some embodiments, cover(s) 106 may be able to withstand internal pressure, such as when a forced-draft fan is used to push gas through photobioreactor unit 100.

Each section 130 may include a separate cover 106 with each cover 106 being connected to adjacent covers when the sections 130 are interconnected. In some embodiments, each section has a support elements 112/114 and a single piece of polyethylene or other suitable material is used to span multiple sections 130.

Each photobioreactor unit 100 may be formed with multiple photobioreactor sections 130 defined, in the illustrated embodiment, by separate cover sections 106. In this manner, constructing the designed length of the photobioreactor unit 100 may be achieved simply by selecting and interconnecting the appropriate number of photobioreactor sections 130. In some embodiments, the length of photobioreactor unit 100 may be changed and the rate of gas and/or liquid flow may be changed to accommodate long-term changes in treatment needs. Additionally, retrofitting photobioreactor unit 100 such as by increasing or decreasing the length may be possible.

Figure 1B:
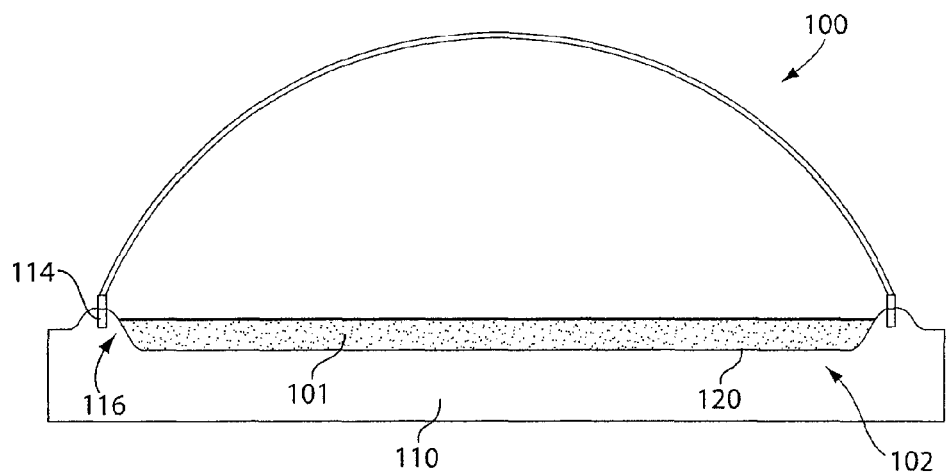
FIG. 1b is a cross-sectional view of one photobioreactor section of a photobioreactor unit according to one embodiment of the invention.

While the photobioreactor unit embodiment shown in FIGS. 1a and 1b includes a trench 102 to create a liquid flow channel, in some embodiments, no trench may be present and the channel for a liquid stream may be formed at or above grade. In certain embodiments, the base comprising the liquid flow channel may not be longitudinally continuous as illustrated, but may comprise a plurality of interconnected sections. For example, in certain embodiments, sections 130 may be defined by both separate a cover section and a separate base section in association with each other. The elevation of the photobioreactor unit may be substantially constant along the entire length of the channel or substantial portions thereof, and gravity flow of the liquid stream may be induced by adding liquid to a first end of the photobioreactor unit and allowing overflow (e.g. over a wall, weir, etc.) at the opposite end. In some embodiments, the photobioreactor unit may have a general, continuous downward pitch to promote liquid flow. In still other embodiments, abrupt elevation drops may be provided at the junctions of photobioreactor sections to create liquid flow and/or a cascading effect and/or to facilitate installation and operation over land areas with more substantial elevation changes.

Cover(s) 106 is shown as a semicircle or other curved surface in many of the embodiments disclosed herein, however, any suitable shape may be used, including a rectangular, triangular or trapezoidal shapes.

Figure 2:
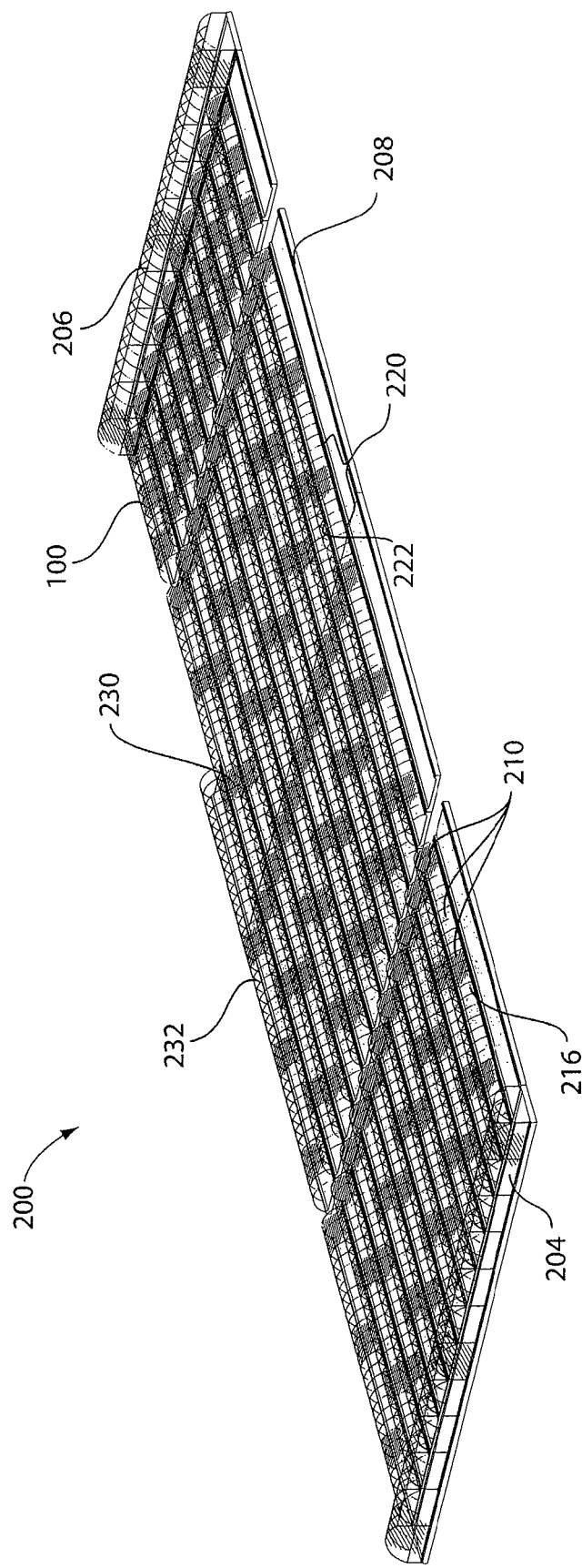
FIG. 2 is a perspective view of a photobioreactor system according to one embodiment of the invention.

Referring now to FIG. 2, one embodiment of a large-scale photobioreactor system 200 is shown in perspective view. In this embodiment, the gas flows in the direction opposite to the liquid stream flow, however, in some embodiments, the gas may flow in the same direction as the liquid stream. Ten parallel photobioreactor units 100 are shown in the embodiment of FIG. 2, but fewer (including a single photobioreactor unit) or more photobioreactor units may be used. While photobioreactor units 100 as illustrated comprise straight, linear segments, in alternative embodiments, one or more of the photobioreactor units may be arcuate, serpentine, or otherwise non-linear, if desired. A liquid inlet/gas outlet bulkhead 204 runs perpendicular to the photobioreactor units at a first end of photobioreactor system 200. At an opposite end of photobioreactor system 200, a liquid outlet/gas inlet bulkhead 206 also runs perpendicular to the photobioreactor units 100. An optional rainwater drainage and vehicle access channel 208 runs parallel to the outer side of the overall photobioreactor system; however, the drainage and vehicle access channel 208 may be positioned between parallel photobioreactor units, or may not be present at all. In some embodiments, smaller rainwater drainage channels which do not accommodate vehicles may be provided.

The lengths of photobioreactor units 100 are selected to be sufficient, for a given desired liquid medium circulation rate, to provide sufficient gas-liquid contact time to provide a desired level of mass transfer between the gas and the liquid medium. Optimal contact time depends upon a variety of factors, especially the algal growth rate and carbon and nitrogen uptake rate as well as feed gas composition and flow rate and liquid medium flow rate. Scalability of the photobioreactor system 200 as a whole may be achieved, for example, by simply by adding additional photobioreactor units to the system, such as by adding photobioreactor units in a parallel relationship to existing photobioreactor units.

As described above, each photobioreactor unit 100 may include various zones having different functionality. One or more photobioreactor sections may be configured as a misting zone 216 to controllably add nutrients/media to the system and facilitate gas-liquid mass transfer. The nutrients and/or the medium in which the nutrients are carried may be provided in certain embodiments at least in part by recycling algae-depleted medium from a dewatering system. More than one nutrient misting section 216 may be provided. By employing a modular section-based construction, channel and/or cover sections which include misters may be added or removed after construction if so desired. In other embodiments, nutrients may be added by methods other than misting such as by direct pumping into the liquid stream. Unrecycled nutrients and/or medium (i.e. fresh make-up) also, or exclusively, may be used to supply the liquid stream in some embodiments.

Of course in some embodiments, nutrients may be added using devices other than misters. For example, nutrients may flow from a pipe into the liquid medium stream, or nutrients may be showered from the top of the photobioreactor unit using a pipe with periodic openings.

Each photobioreactor unit 100 or certain of the photobioreactor units may in certain embodiments include a cooling zone 220 comprising, in certain embodiments, cooling sections 222. As described below with reference to FIG. 5, cooling zone 220 may include portions in which the liquid stream is exposed to the atmosphere to provide for evaporative cooling.

Harvesting algae, adjusting algal concentration, and introducing additional liquid medium can be facilitated via liquid medium inlet bulkhead 204 and liquid medium outlet bulkhead 206. Control of the concentration of algae can be important from the standpoint of maintaining a desirable level of algal growth and proliferation. Algae may be harvested periodically or continuously from an end(s) of the photobioreactor units, or, in some embodiments, from one or more locations located between the ends of the photobioreactor units.

Various devices or mechanisms may in certain embodiments be included within photobioreactor units 100 to increase the interfacial surface area between the gas and the liquid medium to facilitate mass transfer. Sprayers which spray the liquid medium into the gas headspace may be used in some embodiments. In some embodiments, liquid medium may be directed onto or over sheets of plastic or other suitable material such that the liquid medium travels down and/or over the surfaces of the sheets and falls back into the liquid stream. Alternatively or additionally, sheets of material which include pockets may periodically be dipped into the liquid stream and pulled upwardly into the gas headspace to increase the available liquid surface area. In certain embodiments, floating objects and/or devices configured to be partially submerged in the liquid medium (e.g. a paddle wheel) may be used to facilitate enhancement of gas-liquid interfacial area and mass transfer. In certain such embodiments, the objects may be transparent such that they also may act to allow penetration of light to greater depths within the media. In some embodiments, elements may be employed to produce surface ripples or even waves that travel laterally or longitudinally within the liquid medium to increase mass transfer between the gas and the liquid.

At least one or each photobioreactor unit 100 may in certain embodiments include one or more diversion zones or sections 230 which divert portions of the liquid streams to at least one reflow unit such as a reflow channel 232. For example, at least one channel section or zone of a photobioreactor unit may allow liquid to flow perpendicularly to the photobioreactor unit to reach reflow channel 232 (see FIGS. 6a-7). The liquid in the reflow channel may then flow toward to the liquid medium inlet bulkhead 204 and may be added to the liquid inflow by a pump (e.g. an Archimedes screw pump). By recirculating some of the liquid medium comprising phototrophic organisms therein, the addition of new innocula to the liquid medium at the front end of the photobioreactor unit may be reduced or eliminated in certain embodiments. In some embodiments, the recirculation rate may generally be in the range of 0.1-0.95, and preferably in the range of 0.5-0.7.

As would be apparent to those skilled in the art, particular configurations of the various photobioreactor units and components of the photobioreactor system will depend upon the particular use to which the photobioreactor is employed, the composition and quantity of the gas to be treated and other particular parameters specific to individual applications. Given the guidance provided herein and the knowledge and information available to those skilled in the arts of chemical engineering, biochemical engineering, and bioreactor design, one can readily select certain operating parameters and design configurations appropriate for a particular application, utilizing no more than a level of routine engineering and experimentation entailing no undue burden.

As discussed above in the description of FIG. 2, in certain embodiments, photobioreactor system 200 can comprise a plurality of identical or similar photobioreactor units 100 interconnected in parallel. Furthermore, in certain embodiments, at least one or each photobioreactor unit may comprise one photobioreactor section or a plurality of photobioreactor sections in series. Such scalability can provide flexibility to increase the capacity of the photobioreactor system and/or increase the degree of removal of particular components of the gas stream as a particular application or needs demand. In one such embodiment, a photobioreactor system is designed to separate algae species that are efficient in utilizing $NO_x$ from species efficient in utilizing $CO_2$. For example, a nitrogen-efficient algae is placed in a first photobioreactor unit or a first zone of a photobioreactor unit and carbon-efficient algae is placed in a second photobioreactor unit or in a second zone of the same photobioreactor unit in series with the first zone. The flue gas enters the first photobioreactor unit/zone and is scrubbed of nitrogen (from $NO_x$), then flows through the second photobioreactor unit/zone and is scrubbed of carbon (from $CO_2$).

The term "fluidically interconnected", when used in the context of conduits, channels, chambers, or other structures provided herein that are able to contain and/or transport gas and/or liquid, refers to such conduits, channels, containers, or other structures being of unitary construction or connected together, either directly or indirectly, so as to provide a continuous coherent flow path from one conduit or channel, etc. to the other(s) to which they are fluidically interconnected. In this context, two conduits or channels, etc. can be "fluidically interconnected" if there is, or can be established, liquid and/or gas flow through and between the conduits and/or channels (i.e. two conduits/channels are "fluidically interconnected" even if there exists a valve between the two conduits/channels that can be closed, when desired, to impede fluid flow there between).

A channel or trench may comprise, in certain embodiments, fluid impermeable wall(s) for partially or completely surrounding a fluid passing through the channel along its direction of flow. In other embodiments, wall(s) of a channel may only partially surround a fluid passing through the channel along its direction of flow and/or the wall(s) may have some degree of permeability with respect to a fluid flowing in the channel, so long as the wall(s) sufficiently surround the fluid and are fluid impermeable to a sufficient extent so as to be able to establish and maintain a bulk flow direction of fluid generally along a trajectory parallel to a longitudinal axis or curve defining the geometric center of the channel along its length.

The liquid medium contained within the photobioreactor system during operation typically comprises water or a saline solution (e.g. sea water or brackish water) containing sufficient nutrients to facilitate viability and growth of algae and/or other phototrophic organisms contained within the liquid medium. As discussed below, it is often advantageous to utilize a liquid medium comprising brackish water, sea water, or other non-portable water obtained from a locality in which the photobioreactor system will be operated and from which the algae contained therein was derived or is adapted to. Particular liquid medium compositions, nutrients, etc. required or suitable for use in maintaining a growing algae or other phototrophic organism culture are well known in the art. Potentially, a wide variety of liquid media can be utilized in various forms for various embodiments of the present invention, as would be understood by those of ordinary skill in the art. Potentially appropriate liquid medium components and nutrients are, for example, discussed in detail in: Rogers, L. J. and Gallon J. R. "Biochemistry of the Algae and Cyanobacteria," Clarendon Press Oxford, 1988; Burlew 1961; and Round, F. E. The Biology of the Algae. St Martin's Press, New York, 1965; each incorporated herein by reference).

Figure 3:
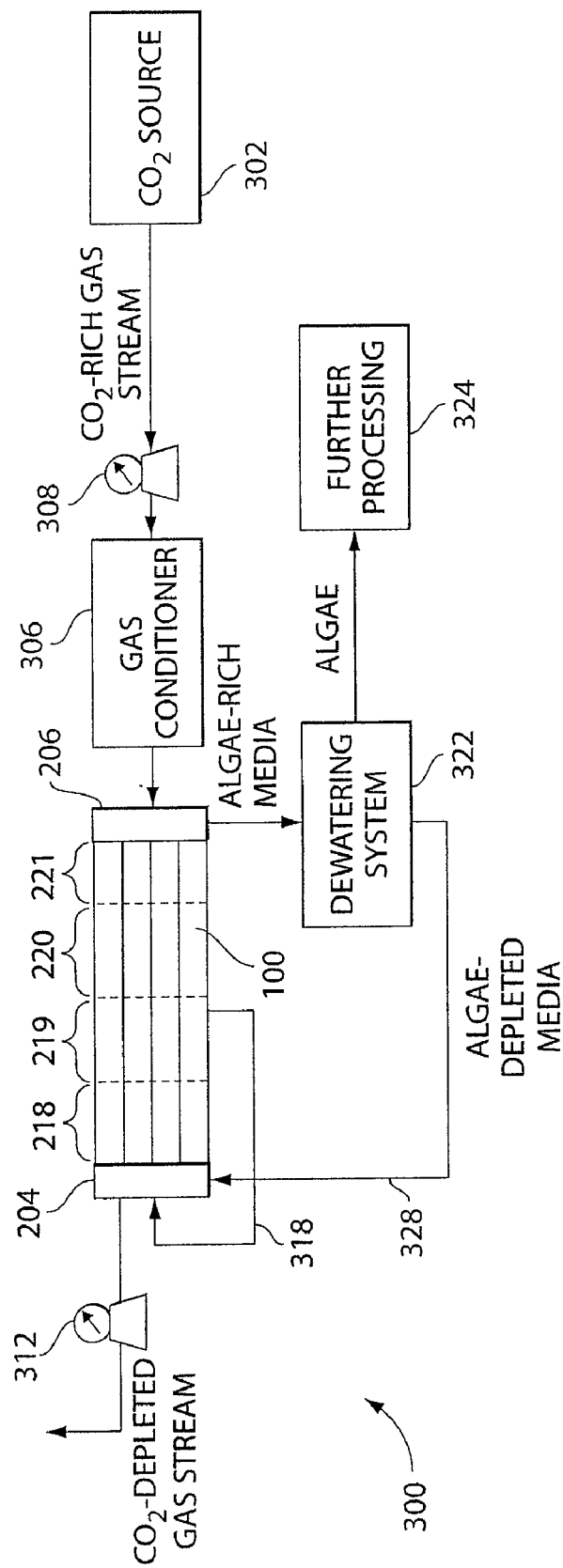
FIG. 3 shows a block diagram of an overall gas treatment/biomass production system comprising a photobioreactor system according to one embodiment of the invention.

FIG. 3 schematically shows one embodiment of a gas treatment/biomas production/photobioreactor system 300 that uses solar energy and photobioreactor system 200 comprising photobioreactor units 100 to produce biomass using a flue gas containing elevated concentrations of carbon dioxide (i.e., gas having a concentration of carbon dioxide greater than ambient air). Flue gas is sent from a $CO_2$ source 302 to a gas conditioner 306, such as a conventional quench zone know to one of skill in the art, to reduce the gas temperature and possibly remove harmful species such as acid gases. In certain embodiments, a forced draft fan 308 may be used to facilitate this transfer of flue gas and/or push gas through photobioreactor units 100, but in some embodiments no forced draft fan is used. The gas is then sent through the photobioreactor units 100 so that the carbon dioxide (and potentially other gases) can interact with a liquid stream in the photobioreactor units to generate biomass. Photobioreactor system 200 may be constructed of one or more photobioreactor units 100 as described above. In the embodiment shown in FIG. 3, the gas is flowed countercurrently to the liquid stream, that is, the liquid stream flow from liquid inlet/gas outlet bulkhead 204 to liquid outlet/gas inlet 206. Make-up liquid medium (not shown) may be added during operation. In some embodiments, for example as described below with reference to FIG. 10, the flow of gas may be co-current with the liquid stream flow.

The photobioreactor units 100 may include different zones, e.g. 218, 219, 220, 221, along the lengths of the various photobioreactor units. In some embodiments, each photobioreactor unit may have similar zones, while in other embodiments, different zones and/or different zone locations may be provided in various of the photobioreactor units. For example, in a first zone 218, the bioreactor may include nutrient addition capabilities such as nutrient misting facilities. A second zone 219 may provide the option of diverting a portion of the liquid flow from the main photobioreactor units so that it may be returned to an upstream zone. Third zone 220 may include cooling capabilities such as evaporative cooling. A fourth zone 221 may be designed and/or controlled to environmentally stress algae, for example to increase lipids production. It should be noted that these particular zones are provided by way of example only, and as described further below, photobioreactor system 200 and/or individual photobioreactor units within photobioreactor system 200 may include fewer or more zones.

$CO_2$-depleted gas exits photobioreactor units 100 through liquid inlet/gas outlet bulkhead 204 and may be vented to the atmosphere or passed to further treatment options. An induced-draft fan 312 may be used to pull gas through the bioreactor, or, as described above, a forced-draft fan 308 may be used upstream of the photobioreactor units 100 instead of or in addition to the induced-draft fan in some embodiments. By using an induced-draft fan, the photobioreactor system and/or other portions of the overall system may be maintained at a negative pressure, thereby reducing the risk of unintentional venting of untreated gases to the atmosphere. Additionally, the use of an induced-draft fan (e.g., a blower), may simplify the integration of a photobioreactor system with existing power plants thereby reducing disruptions to power plant operations. A blower is considered to be fluidically connected to a photobioreactor unit even if it is not directly connected to the photobioreactor unit, that is, other pieces of equipment or other conduits may be connected between the photobioreactor unit and the blower.

In certain embodiments, a portion of the liquid stream may be diverted, as shown by arrow 318, from a downstream zone of the photobioreactor units 100 and returned to an upstream zone (or in some embodiments to liquid inlet/gas outlet bulkhead 204) which may provide some of the benefits of a "back-mixed" reactor system. In this regard, the amount of inoculum added to the liquid in the photobioreactor units may be reduced or eliminated. Additionally, overall average residence time for the liquid medium may be increased without extending the length of the photobioreactor units. The diverted liquid medium may be returned at a position and in a manner such that the returned liquid medium causes or increases turbulence in the liquid stream, which may enhance heating or cooling and/or photomodulation in certain photobioreactor unit sections.

Figure 5:
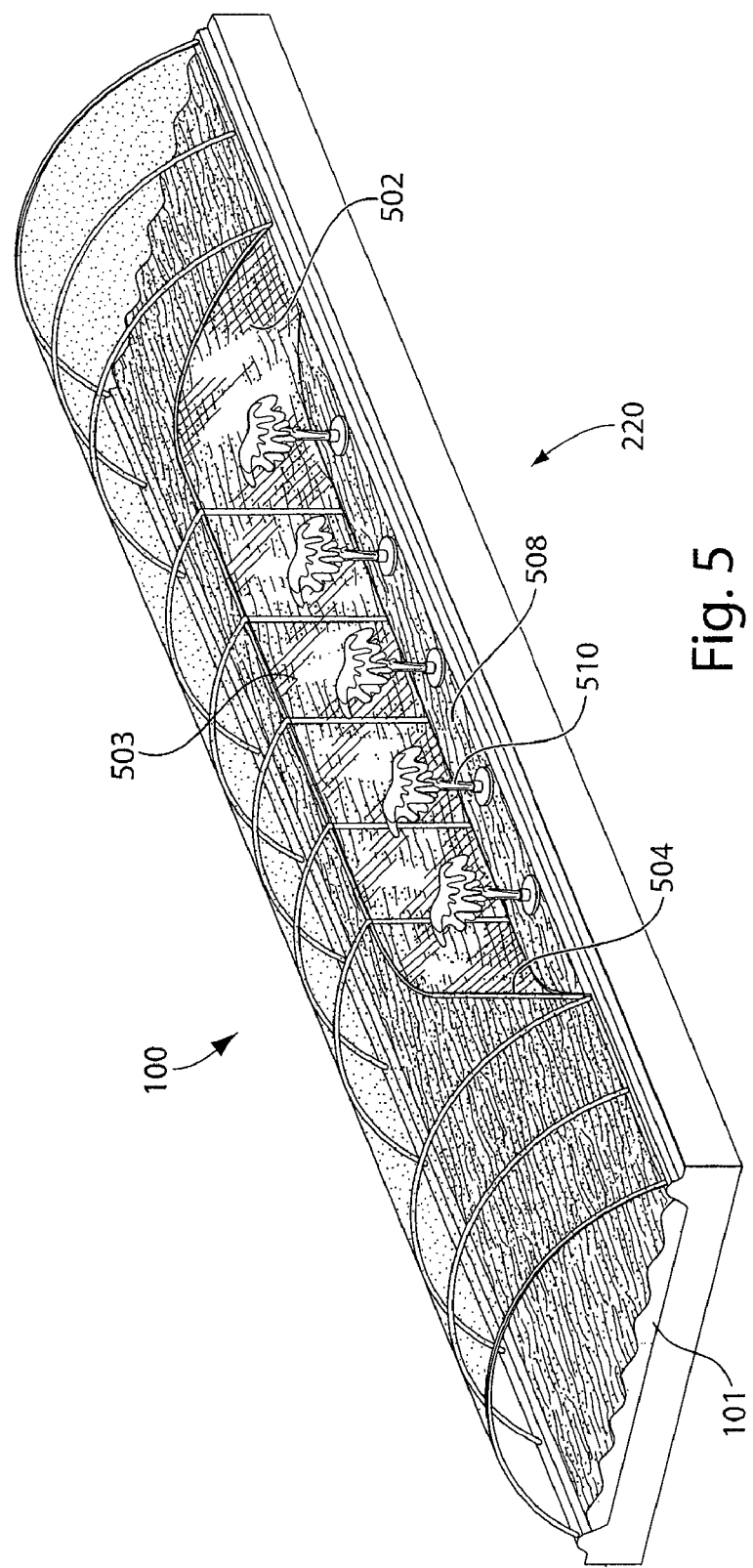
FIG. 5 is a perspective view of an evaporative cooling zone of a photobioreactor unit according to one embodiment of the invention.

As mentioned above, photobioreactor units 100 also may include a cooling zone(s) 220 such as an evaporative cooling zone. In some embodiments, while flowing through photobioreactor unit 100, the liquid stream temporarily exits the enclosed portion of the photobioreactor unit and is exposed to the atmosphere. Evaporation of some of the liquid cools the remaining liquid, which then reenters the enclosed portion of the photobioreactor unit 100. Each photobioreactor unit may be constructed and arranged such that the liquid stream does not significantly change direction or speed when exiting and reentering the enclosed portion of the photobioreactor unit. For example, as shown in FIG. 5, one or more photobioreactor sections of a photobioreactor unit may include walls that reduce the amount of cross-sectional area available for gas flow, but provide an area where the cover section(s) may be removed or indented, as shown, to allow exposure of the liquid stream to the atmosphere.

In some embodiments of evaporative cooling zones, a portion of the liquid stream may be continuously exposed to the atmosphere, that is, for a relatively long zone of the photobioreactor unit, which may be made up of a large number of photobioreactor sections, the zone, or each section comprising such zone, may include an area (for example on the lateral side of the trench) that provides an evaporative cooling area. Substantially continuous mixing of the exposed portion of the liquid stream with the unexposed portion of the liquid stream may provide adequate cooling for the reactor.

The photobioreactor sections and/or units may be heated and maintained at certain temperatures or temperature ranges suitable or optimal for productivity. These specific, desirable temperature ranges for operation will, of course, depend upon the characteristics of the phototrophic species used within the photobioreactor systems, the type of photobioreactor, etc. Typically, it is desirable to maintain the temperature of the liquid medium between about 5 degrees C. and about 45 degrees C., more typically between about 15 degrees C. and about 37 degrees C., and most typically between about 15 degrees C. and about 25 degrees C. For example, a desirable temperature operating condition for a photobioreactor utilizing *Chlorella* algae could have a liquid medium temperature controlled at about 30 degrees C. during the daytime and about 20 degrees C. during nighttime. In one embodiment, the temperature of the photobioreactor is maintained at about 20 degrees C.

In certain embodiments, the temperature, velocity, residence time, depths and/or nutrient concentrations can be maintained at different levels/values in the various zones to control for different factors and/or provide particular functionality. For example, it is possible in certain embodiments to maintain one zone so as to maximize growth rates and to maintain conditions in another zone to maximum lipids production.

Algae-rich liquid exiting from photobioreactor system 200 may be sent to a dewatering system 322. Various conventional methods and/or systems of dewatering may be used to dewater the algae, including dissolved air floatation and/or tangential flow filtration, or any other suitable dewatering approach.

The dewatered algae may be sent for further processing 324, for example, drying. Dried algal biomass can be used directly as a solid fuel for use in a combustion device or facility and/or could be converted into a fuel grade oil (e.g., biodiesel) and/or other fuel (e.g., ethanol, methane, hydrogen). The algae also may be used as food supplements for humans and animals. In certain embodiments, at least a portion of the biomass, either dried or before drying, can be utilized for the production of products comprising organic molecules, such as fuel-grade oil (e.g. biodiesel) and/or organic polymers. Methods of producing fuel grade oils and gases from algal biomass are well known in the art (e.g., see, Dote, Yutaka, "Recovery of liquid fuel from hydrocarbon rich micro algae by thermo chemical liquefaction," *Fuel*. 73:Number 12. (1994); Ben-Zion Ginzburg, "Liquid Fuel (Oil) From Halophilic Algae: A renewable Source of Non-Polluting Energy, Renewable Energy," Vol. 3, No 2/3. pp. 249-252, (1993); Benemann, John R. and Oswald, William J., "Final report to the DOE: System and Economic Analysis of Micro algae Ponds for Conversion of $CO_2$ to Biomass." DOE/PC/93204-T5, March 1996; and Sheehan et al., 1998; each incorporated by reference).

Algae-depleted medium resulting from dewatering operations may be disposed of or may be returned to photobioreactor system 200 (after optionally being mixed with fresh liquid medium), as shown by arrow 328, to return unused nutrients to the system. Such an approach may reduce the amount of fresh water and nutrients to be added to the system.

In some embodiments, other processes of the photobioreactor system may be integrated with the power plant or other $CO_2$ source. For example, the hot flue gas from the power plant may be used to at least partially dry the biomass produced by the photobioreactor system.

Algae, or other phototrophic organisms, may, in certain embodiments, be pre-adapted and/or pre-conditioned to specific environmental and operating conditions expected to be experienced in a full scale photobioreactor system of the invention during use. Methods and apparatus for adaptation and pre-conditioning algae may be found in commonly-owned International Application Publication No. WO 2006/020177, which is hereby incorporated by reference in its entirety.

Although photobioreactor system 200 is described as being utilized with natural sunlight, in alternative embodiments, an artificial light source providing light at a wavelength able to drive photosynthesis may be utilized in supplement to or instead of natural sunlight. For example, a photobioreactor utilizing both sunlight and an artificial light source may be configured to utilize sunlight during the daylight hours and artificial light in the night hours, so as to increase the total amount of time during the day in which the photobioreactor system can convert $CO_2$ to biomass through photosynthesis.

Since different types of algae can require different light exposure conditions for optimal growth and proliferation, in certain embodiments, especially those where sensitive algal species are employed, light modification apparatus or devices may be utilized in the construction of the photobioreactors according to the invention. Some algae species either grow much more slowly or die when exposed to ultraviolet light. If the specific algae species being utilized in the photobioreactor is sensitive to ultraviolet light, then, for example, certain portions of cover(s) 106, or alternatively, the entire cover outer and/or inner surface, could be coated or covered with one or more light filters that can reduce transmission of the undesired radiation. Such a light filter can readily be designed to permit entry into the photobioreactor system of wavelengths of the light spectrum that the algae need for growth while barring or reducing entry of the harmful portions of the light spectrum. Such optical filter technology is already commercially available for other purposes (e.g., for coatings on car and home windows). A suitable optical filter for this purpose could comprise a transparent polymer film optical filter such as SOLUS™ (manufactured by Corporate Energy, Conshohocken, Pa.). A wide variety of other optical filters and light blocking/filtering mechanisms suitable for use in the above context will be readily apparent to those of ordinary skill in the art. In certain embodiments, especially for photobioreactor systems utilized in hot climates, as part of a temperature control mechanism, a light filter comprising an infrared filter could be utilized to reduce heat input into the photobioreactor system, thereby reducing the temperature rise in the liquid medium.

Figure 4:
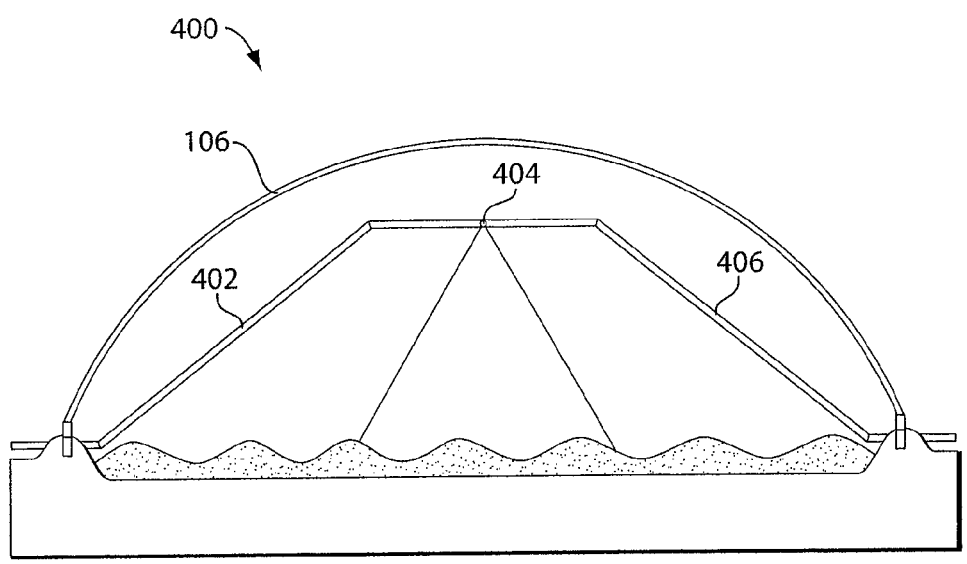
FIG. 4 is a cross-sectional view of a nutrient misting section of a photobioreactor unit, according to one embodiment of the invention.

Referring now to FIG. 4, one embodiment of a nutrient/medium misting photobioreactor section or zone 400 is illustrated. A liquid inlet 402 may be formed of a conduit that also provides support for a mister 404. In some embodiments, liquid may flow into inlet 402 and all of the liquid may exit through mister 404. In some embodiments, liquid may flow through inlet 402 and some of the liquid may exit through mister 404 while the remaining liquid exits through an outlet 406 on the opposite side of section or zone 400 and continues to an adjacent photobioreactor unit. Mister 404 is shown as spraying liquid downwardly in FIG. 4, but in some embodiments the liquid may be aimed upwardly toward the inside of cover 106, such as directly upwardly. In this manner, mister 404 or other liquid injection device may help to clean the inside of cover 106 and the thin film of liquid formed on the inside surface of the cover can further enhance gas-liquid mass transfer.

FIG. 5 shows a perspective view of one embodiment of a cooling zone 220 for a photobioreactor unit 100. In this embodiment, cover(s) 106 forms three walls 502, 503, 504 which reduce the cross-sectional area of the gas headspace. Each wall 502, 503, 504 penetrates into liquid stream 101 such that photobioreactor unit 100 remains gas-tight. Walls 502, 503, 504 may not, however, in certain embodiments reach the base of photobioreactor unit 100, such that, therefore, in such embodiments, the liquid stream may readily flow into evaporative cooling area 508. In some embodiments, sprayers 510 or other devices which increase surface area exposure of the liquid stream to the atmosphere may be employed to enhance evaporative cooling.

While evaporative cooling area 508 is shown to be present only on one side of the photobioreactor unit in this embodiment, a second evaporative cooling area may additionally (or instead) be provided on the opposite side of the photobioreactor unit, or positioned at an intermediate location positioned between the two laterally opposed sides of photobioreactor unit 100. For embodiments in which cooling zone 220 comprises one or more interconnectable photobioreactor sections, as with photobioreactor sections that include nutrient misters for embodiments including such photobioreactor sections, the interchangeability of the photobioreactor sections may allow for the addition or subtraction of cooling areas after installation of the photobioreactor system.

Figure 6A:
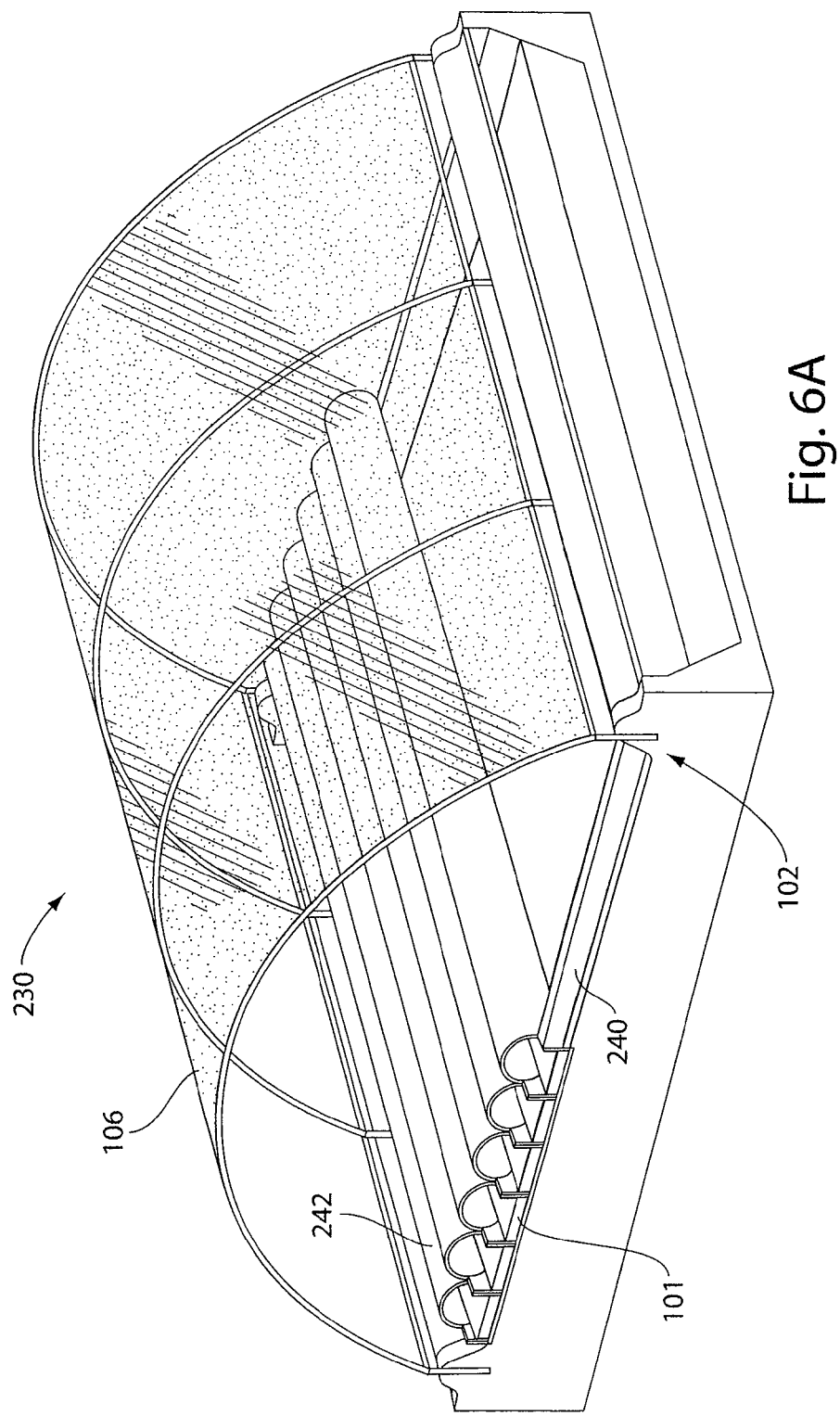
FIG. 6a is a perspective view of a first configuration of a photobioreactor unit zone for diverting liquid to a reflow channel.
Figure 6B:
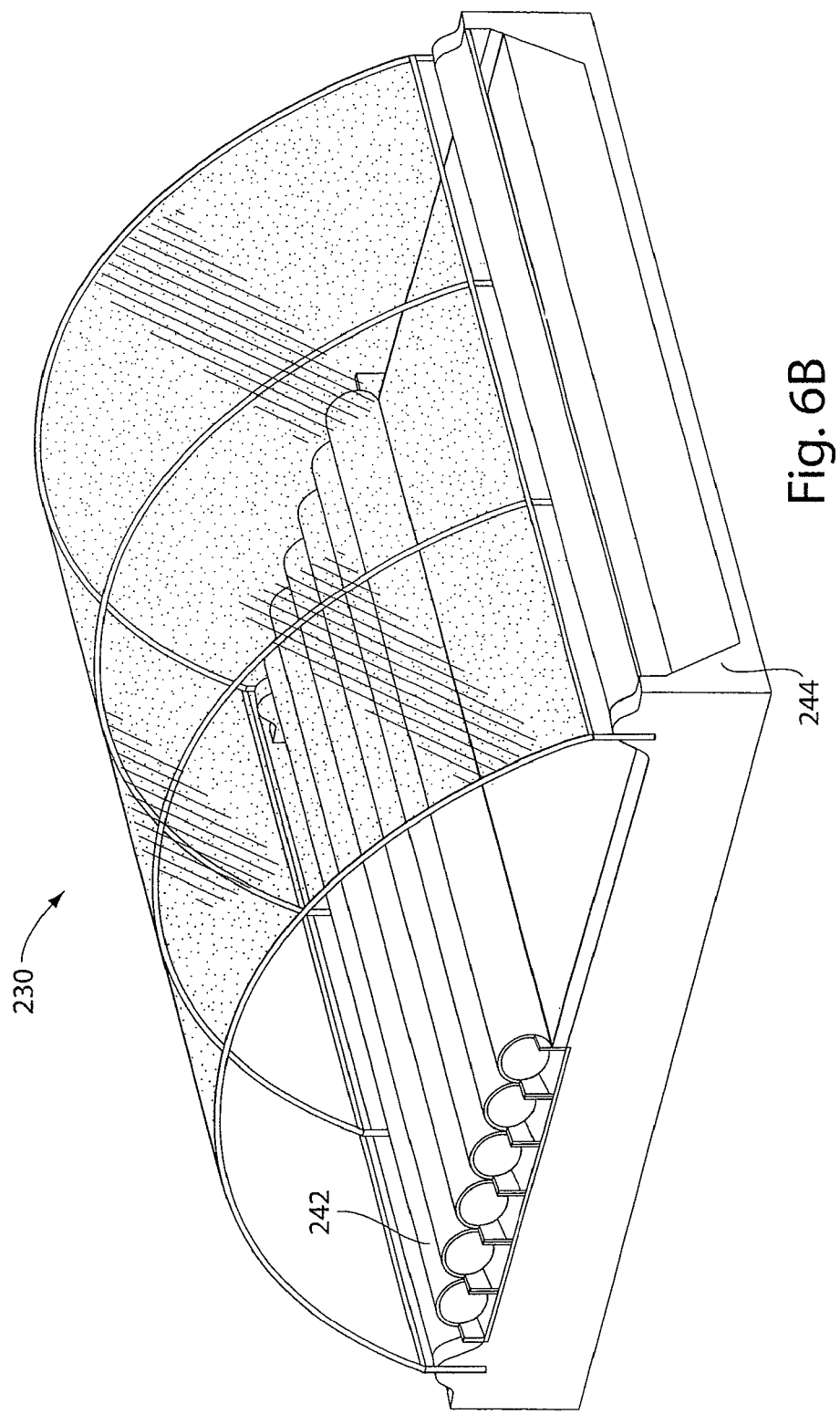

One embodiment of a liquid flow diversion photobioreactor section or zone 230 is illustrated in FIGS. 6a and 6b. As shown in FIG. 6a, a movable weir 240 may be deployed such that all liquid in the photobioreactor unit liquid stream 101 is directed through bypass conduits 242. In such a configuration, none of the liquid flowing through diversion photobioreactor section or zone 230 is diverted, and all of the liquid medium flowing through the section continues toward the liquid medium outlet. With the movable weir 240 lowered, as shown in FIG. 6b, a portion of the liquid medium is diverted into a transverse channel 244 which flows to a reflow channel such as reflow unit 232 illustrated in FIG. 2. In some cases, all of the liquid stream is diverted depending on the relative heights of bypass conduits 242, adjustable weir 240 and the liquid levels in trench 102 and transverse channel 244. In certain embodiments, the degree of diversion is controllable either or both of manually or through use of a computer operated process control system.

A controller, e.g. a computer-implemented system, may be used to monitor and control the operation of the various components of the photobioreactor sections, units and systems disclosed herein, including valves, sensors, weirs, blowers, fans, dampers, pumps, etc. Certain embodiments may employ computer systems and methods described in commonly-owned International Publication No. WO2006/020177, particularly with reference to FIG. 7A of that publication. In addition to automating operation of aspects of the photobioreactor system, use of a computer-implemented system may facilitate optimizing or improving the efficiency of the system by determining suitable values for various control parameters. In some embodiments, flow may be controlled to provided a desired level of turbulence and light/dark exposure intervals for improved growth, and described and determined according to methods also described in International Publication No. WO2006/020177.

Figure 7:
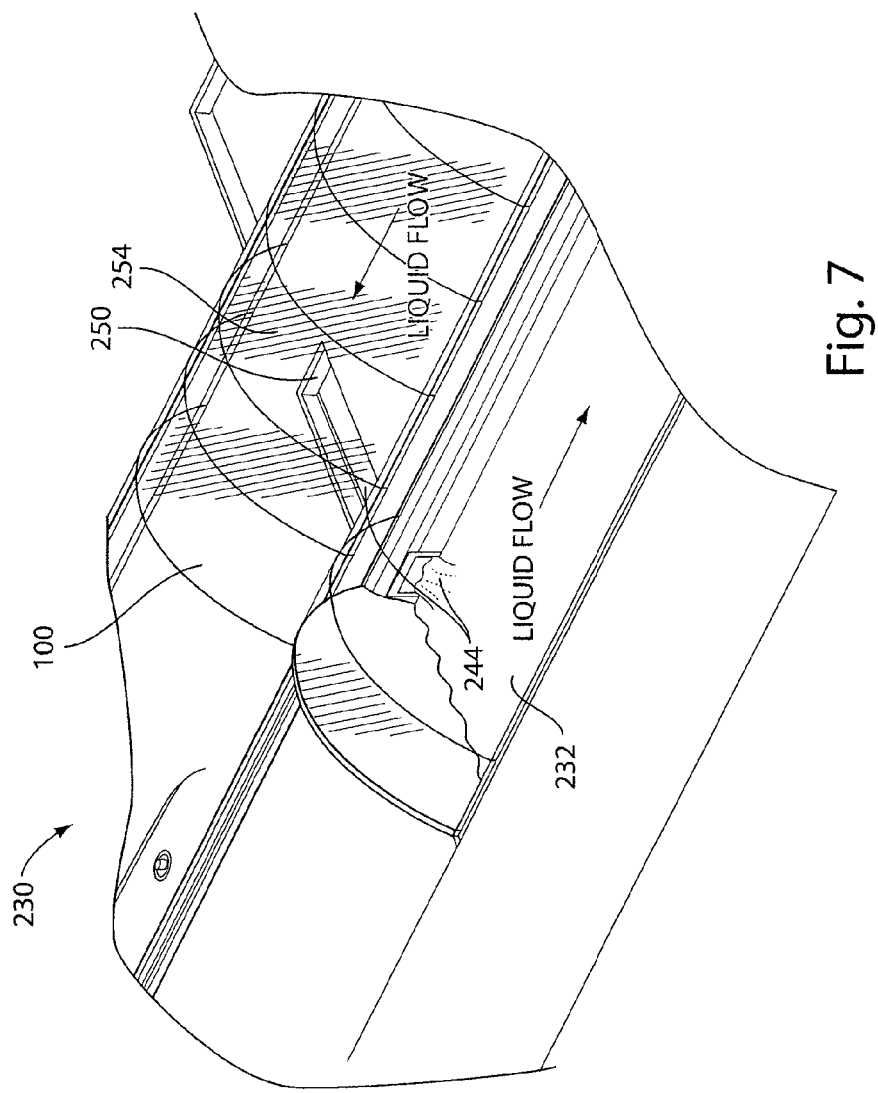
FIG. 7 is a perspective view of two photobioreactor unit zones configured to divert liquid to a reflow channel, according to one embodiment of the invention.

FIG. 7 shows another embodiment of a diversion photobioreactor section or zone 230. In this embodiment, an adjustable weir 250 may be lowered to allow liquid medium to flow into transverse channel 244. When adjustable weir 250 is raised, the liquid medium flows through a bypass portion 254 of diversion zone 230 to continue along the photobioreactor unit.

Figure 8B:
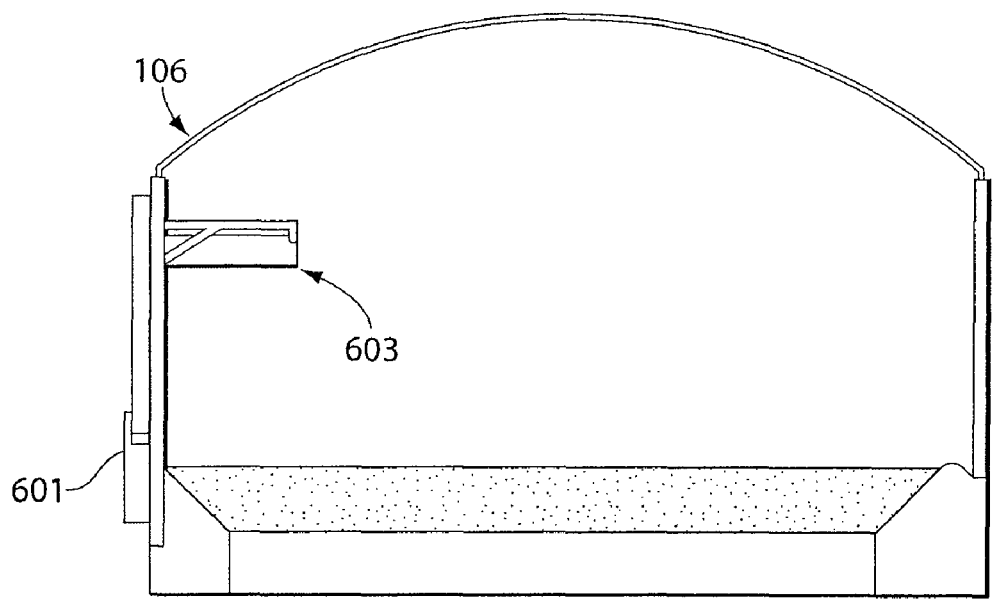
Figure 9:
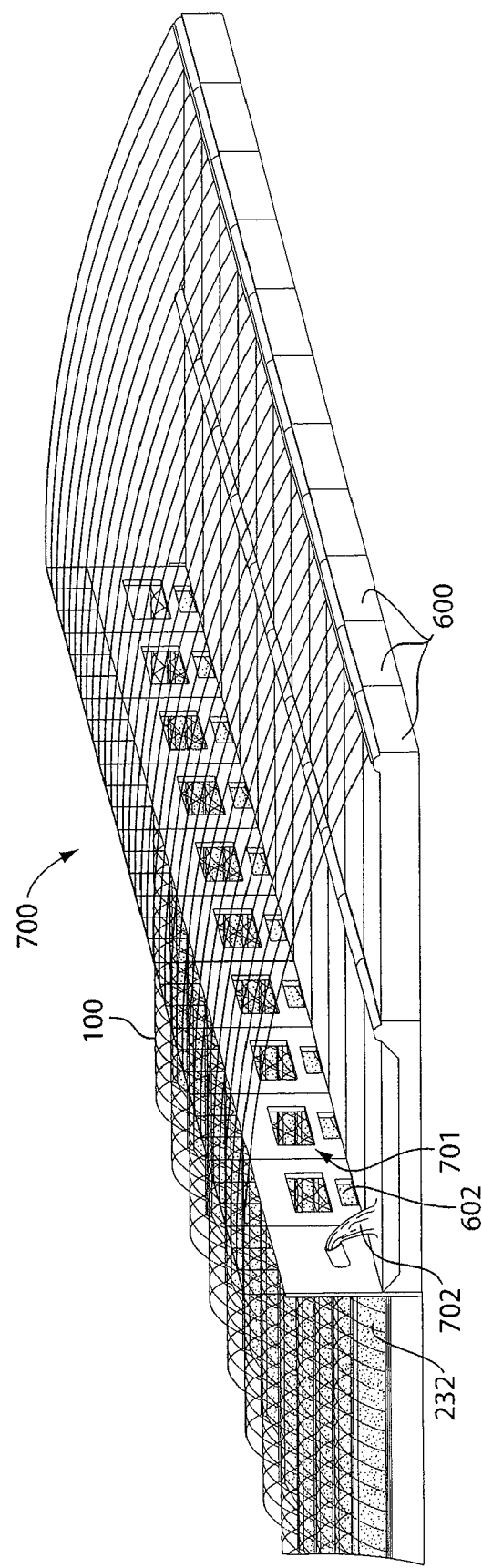
FIG. 9 is a perspective view of a bulkhead distribution channel operatively connected with ten photobioreactor units according to one embodiment of the invention.

One embodiment of a liquid and gas bulkhead zone 600 is shown in FIGS. 8a-8b. In certain embodiments, a series of sections 600 may be connected end to end and travel transversely to a plurality of parallel photobioreactor units, as shown in FIG. 9. Each bulkhead section 600 may include an automated weir 601 or other liquid control element for adjustably controlling the size and elevation of a liquid passageway 602. Each bulkhead section 600 also may include a flue gas damper 603 or other flue gas control element for controlling the size of a gas passageway 604. An embossing 606 or ridge for attachment to a photobioreactor unit may be provided on a side of bulkhead section 600. The sizes of liquid passageway 602 and gas passageway 604 may be fixed or adjustable. For example, in a system with a consistent liquid stream flow rate, the weirs for each of a plurality of photobioreactor units may be permanently set such that flow from the bulkheads is substantially equal for each photobioreactor unit. In other embodiments, each bulkhead section may include an adjustable weir so that the flow of liquid to each photobioreactor unit can be independently controlled. Similarly, gas passageways may be designed to equally distribute gas flow amongst all of the photobioreactor units, or, gas dampers may be configured and/or operated so that gas flow to each photobioreactor unit may be independently controlled. At least one cover 610 for the bulkhead section(s) may be transparent and otherwise similar to the covers for the photobioreactor units, or, in some embodiments, the cover may be opaque and/or made of a different material than the photobioreactor unit covers.

Ten bulkhead sections 600 are shown interconnected in FIG. 9 to form a bulkhead distribution unit 700. The open lateral inlet 701 to the gas head space of the bulkhead provides an inlet for flue gas that may be fluidically interconnected with a conduit(s) supplying feed gas from a $CO_2$ source and/or gas conditioner 306 and/or quench zone of the system (discussed below). Recirculated liquid 702 from a reflow channel 232 is shown being pumped into bulkhead distribution unit 700. The recirculated liquid 702 mixes with fresh liquid medium and/or liquid being recycled from dewatering operations, and the liquid is distributed to the various photobioreactor units 100 by gravity flow through liquid passageways 602.

Although not shown, dampers, such as guillotine dampers, between one or more bulkhead sections may be used to limit gas and/or liquid flow to certain photobioreactor units. A guillotine damper and/or other flow control element may also be used within a single point entry to the bulkhead region so that all flow of gas and/or liquid may easily be stopped.

While many of the embodiments described herein employ the movement of liquid through a gas headspace to promote mass transfer between the gas and liquid, in certain embodiments, additionally or alternatively, gas may be sparged into the liquid. For example, while the bulk of gas distribution into the liquid medium present in a photobioreactor unit 100 may be through a gas passageway such as the one shown in FIG. 1a, a not insignificant amount of gas may be sparged into the liquid medium in certain embodiments. The sparging, in addition to creating an additional gas-liquid interface, may create turbulence or additional turbulence in certain regions where such turbulence is desirable.

Figure 10:
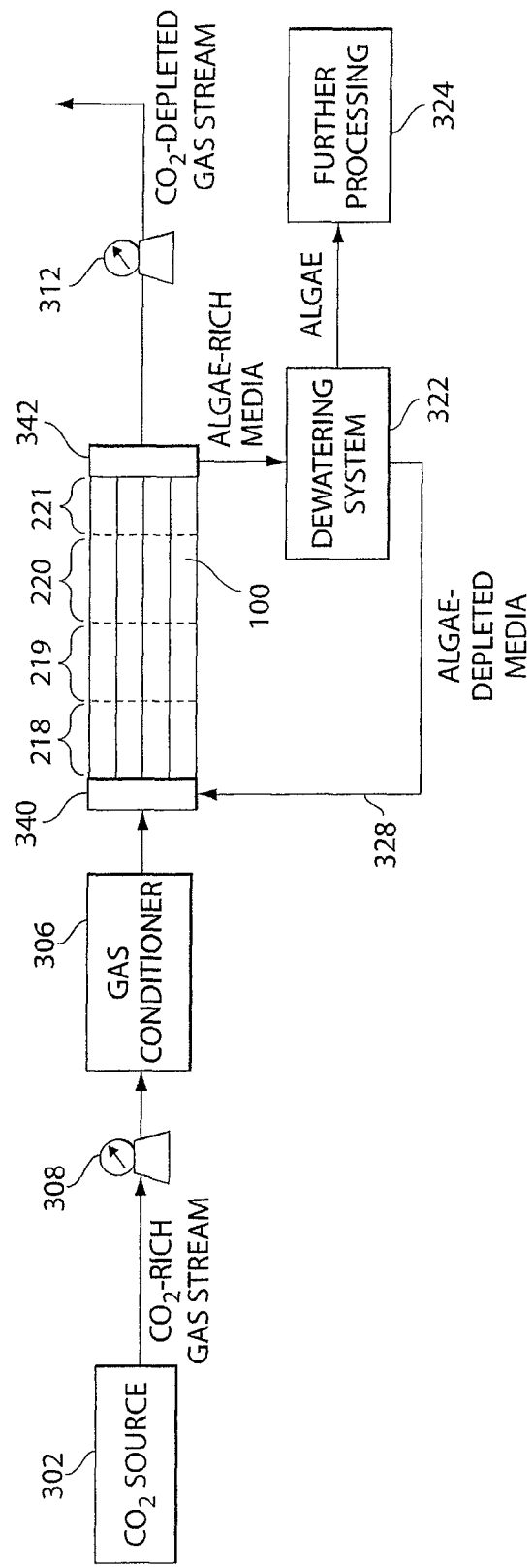
FIG. 10 is a block diagram of an overall gas treatment/biomass production system comprising a photobioreactor system according to an alternative embodiment of the invention.

In an alternate embodiment of the invention, a photobioreactor system may include some or all of the elements of the photobioreactor system shown and described in FIG. 3, with the exception of the recycle for recirculating liquid from downstream in a photobioreactor unit to upstream in the photobioreactor unit. FIG. 10 shows one embodiment of such a system, which may include many of the same elements as the system described above with reference to FIG. 3. Additionally, FIG. 10 illustrates an embodiment in which gas flows co-currently with liquid flow through photobioreactor units 100. Thus, both liquid and gas flow from a liquid inlet/gas inlet bulkhead 340 to a liquid outlet/gas outlet bulkhead 342 in this embodiment.

Figure 11:
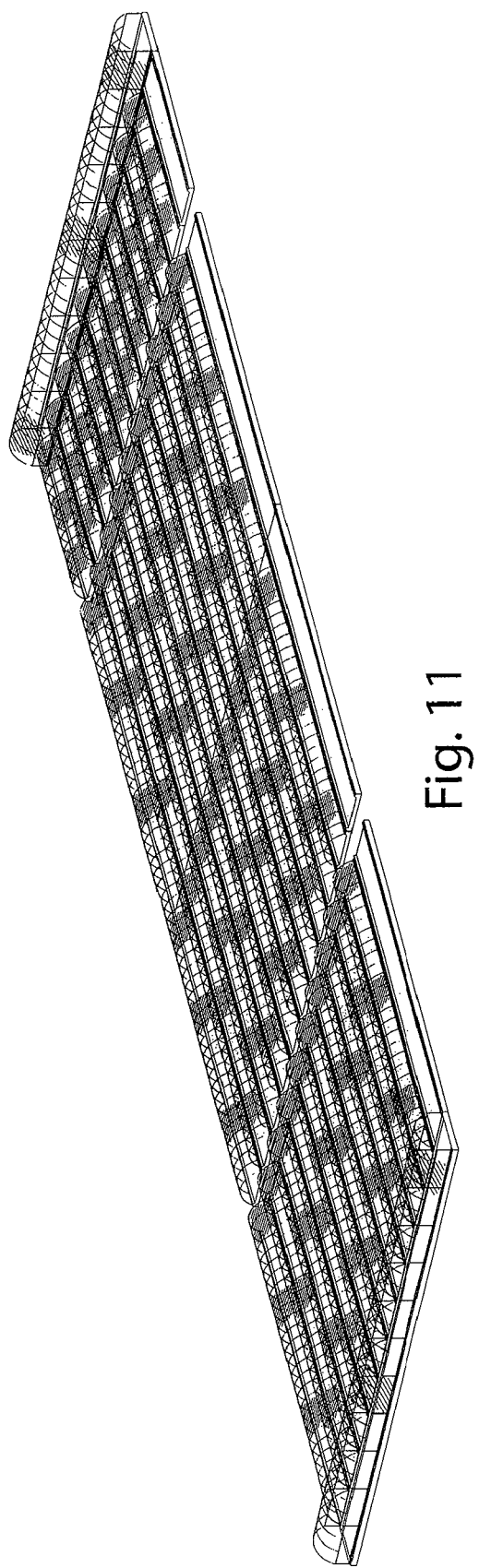
FIG. 11 is a perspective view of a photobioreactor system according to an alternative embodiment of the invention.

A perspective view of one physical embodiment of the photobioreactor system 700 illustrated in FIG. 10 is shown in FIG. 11.

In many current photobioreactor systems, chosen, desirable strains of algae can be difficult to maintain in a photobioreactor that is not scrupulously sterilized and maintained in a condition that is sealed from the external environment. The reason for this is that the algal strains being used in such photobioreactors are not well adapted or optimized for the conditions of use, and other, endemic algal strains in the atmosphere are more suitably conditioned for the local environment, such that if they have the ability to contaminate the photobioreactor they will tend to predominate and eventually displace the desired algae species. Such phenomena may be mitigated and/or eliminated by using adaptation protocols and algal cultures described in International Publication No. WO2006/020177 A1, published on Feb. 23, 2006, which is hereby incorporated herein in its entirety. Use of such protocols and algae strains produced by such protocols may not only increase productivity and longevity of algal cultures in real photobioreactor systems, thereby reducing capital and operating costs, but also may reduce operating costs by reducing or eliminating the need to sterilize and environmentally isolate the photobioreactor system prior to and during operation, respectively.

Many power plants include ponds or other bodies of water to which waste heat is discharged. In some embodiments, especially in colder climates, a photobioreactor may be positioned on top of a wastewater pond to achieve one or more possible advantages. By floating or otherwise positioning a bioreactor on a body of water, the photobioreactor system may take advantage of the inherent flatness of the surface of a body of water over an expansive area. Further, by using an already existing pond, limited additional geographic area is required for the photobioreactor system. If the body of water accepts heated wastewater from the power plant (or other source) the photobioreactor system can be heated by the body of water to improve biomass production and/or prevent freezing in cold ambient conditions.

Figure 12:
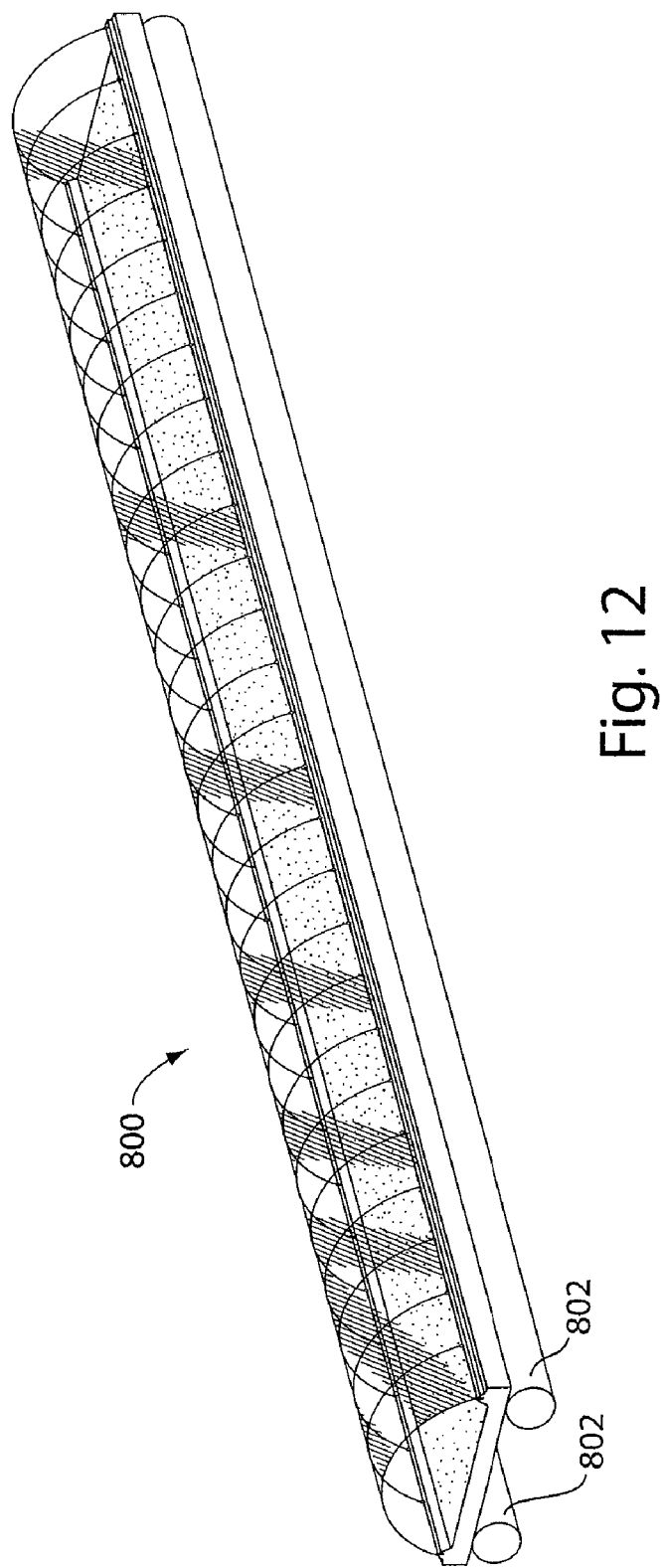
FIG. 12 shows a cross-sectional view of a photobioreactor unit adapted to float on a water body.

One embodiment of a photobioreactor unit 800 adapted for positioning on a body of water is shown in FIG. 12. Photobioreactor unit 800 is supported by two pontoon floats 802 that extend longitudinally along the length of the photobioreactor unit. Of course, other structures may be used to float or support one or more photobioreactor units on a body of water.

To accommodate rain water and/or melted snow runoff, a drain system (not shown) may be incorporated into any of the above described photobioreactor systems. In one embodiment of a drainage system, a drainage hole is provided periodically along a collection channel positioned between two photobioreactor units of the photobioreactor system. The drainage hole empties into a drainage conduit that transversely spans each of the photobioreactor units that are positioned side-by-side. The drainage conduit leads to a drainage trench to lead water away from the photobioreactor system. In some embodiments, the drainage trench may be wide enough to accommodate various vehicles (e.g. vehicle access channel 208 of FIG. 2 may comprise a drainage trench).

Figure 13:
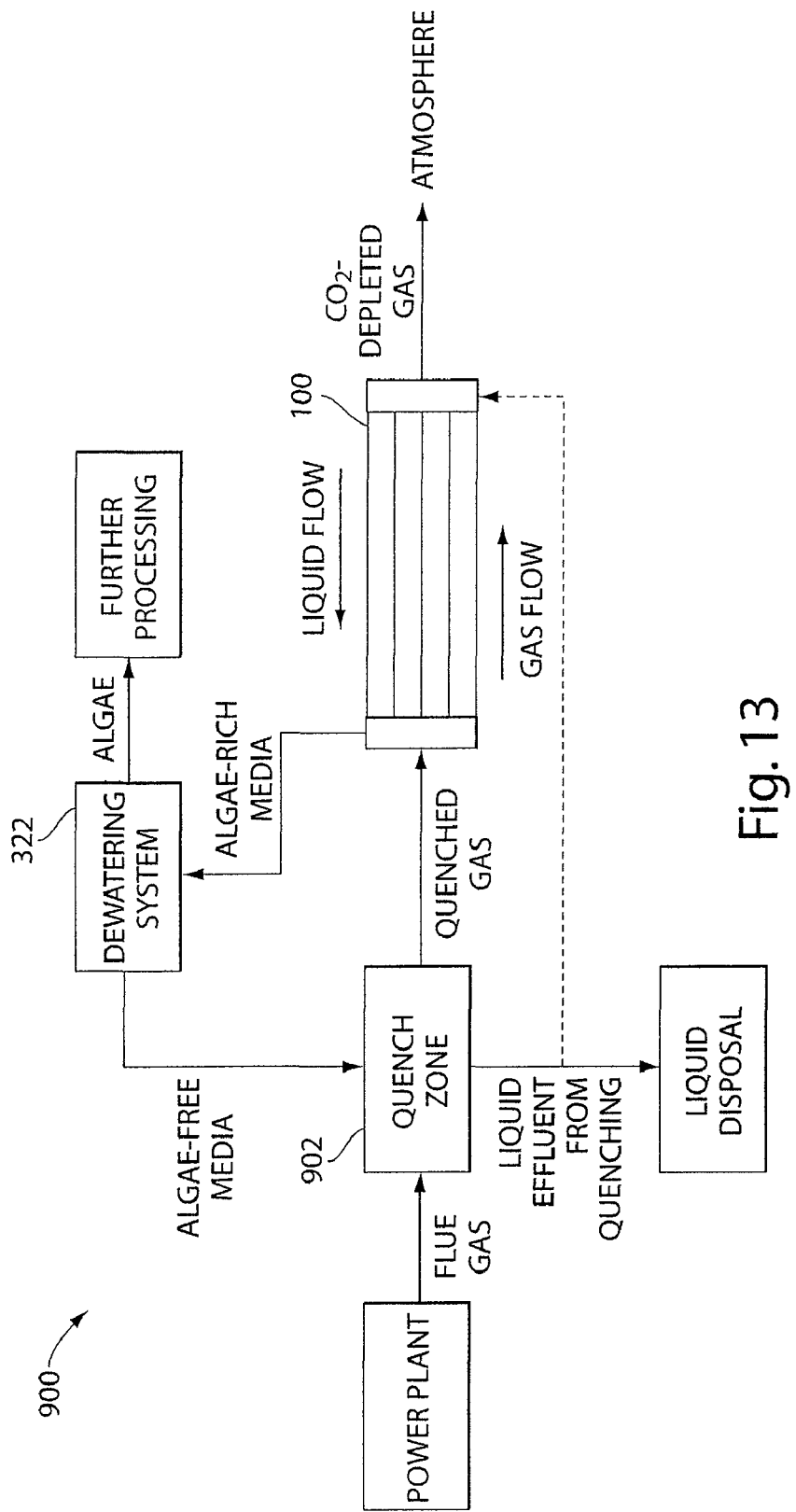
FIG. 13 is a block diagram of an overall gas treatment/biomass production system comprising a photobioreactor system which uses liquid associated with the system to quench flue gas.

In certain embodiments, advantageously, hot flue gas being received from a power plant may be cooled and/or scrubbed to remove undesirable components with liquid that is used as part of the photobioreactor system according to some embodiments of the invention. For example, as illustrated in FIG. 13, in some embodiments of a gas gas treatment system 900, algae-free medium that results from dewatering operations may be sprayed in a quench zone 902 to cool/scrub hot flue gas before the gas enters photobioreactor system 200 comprising photobioreactor units 100. Liquid effluent from quench zone 902 may be disposed of, or in some embodiments, returned to photobioreactor units 100 (dashed line).

Using liquid medium to quench the flue gas heats the medium and may reduce the pH of the medium. One or both of these effects may help kill adventitious biological species, such as rotofers, cilitates, bacteria, and viruses that may impair the growth of the desired algae. If the quench effluent stream is returned to the system upstream of the dewatering step, it may improve the dewatering operation. For example, reducing the pH of the dewatering feed may improve the effectiveness of polycationic coagulants and alum-based flocculants. Additionally, thermally heating the algae-containing media may induce necrosis and autoflocculation, which simplifies the dewatering process and may reduce or eliminate the need for chemical additives.

Figure 14:
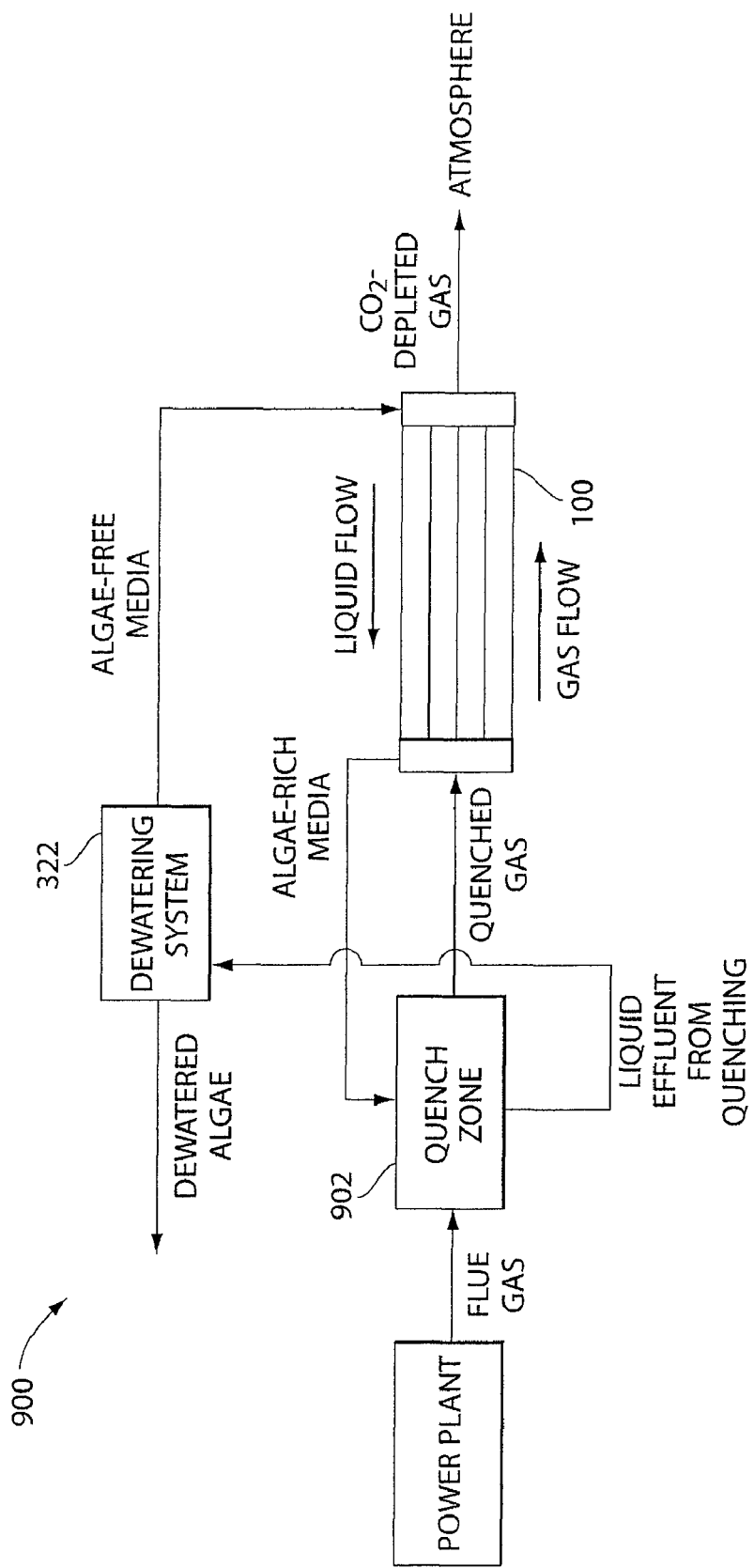
FIG. 14 is a block diagram of an overall gas treatment/biomass production system comprising a photobioreactor system which used liquid associated with the system to quench flue gas.

In an alternative embodiment illustrated in FIG. 14, algae-rich medium harvested from the outlet of photobioreactor units 100 may be used in quench zone 902 to cool flue gas. The liquid effluent from quench zone 902 may then be sent to dewatering system 322 to enrich the algae. As with some other embodiments described herein, algae-free medium from dewatering system 322 may optionally be returned to photobioreactor units 100.

Figure 15:
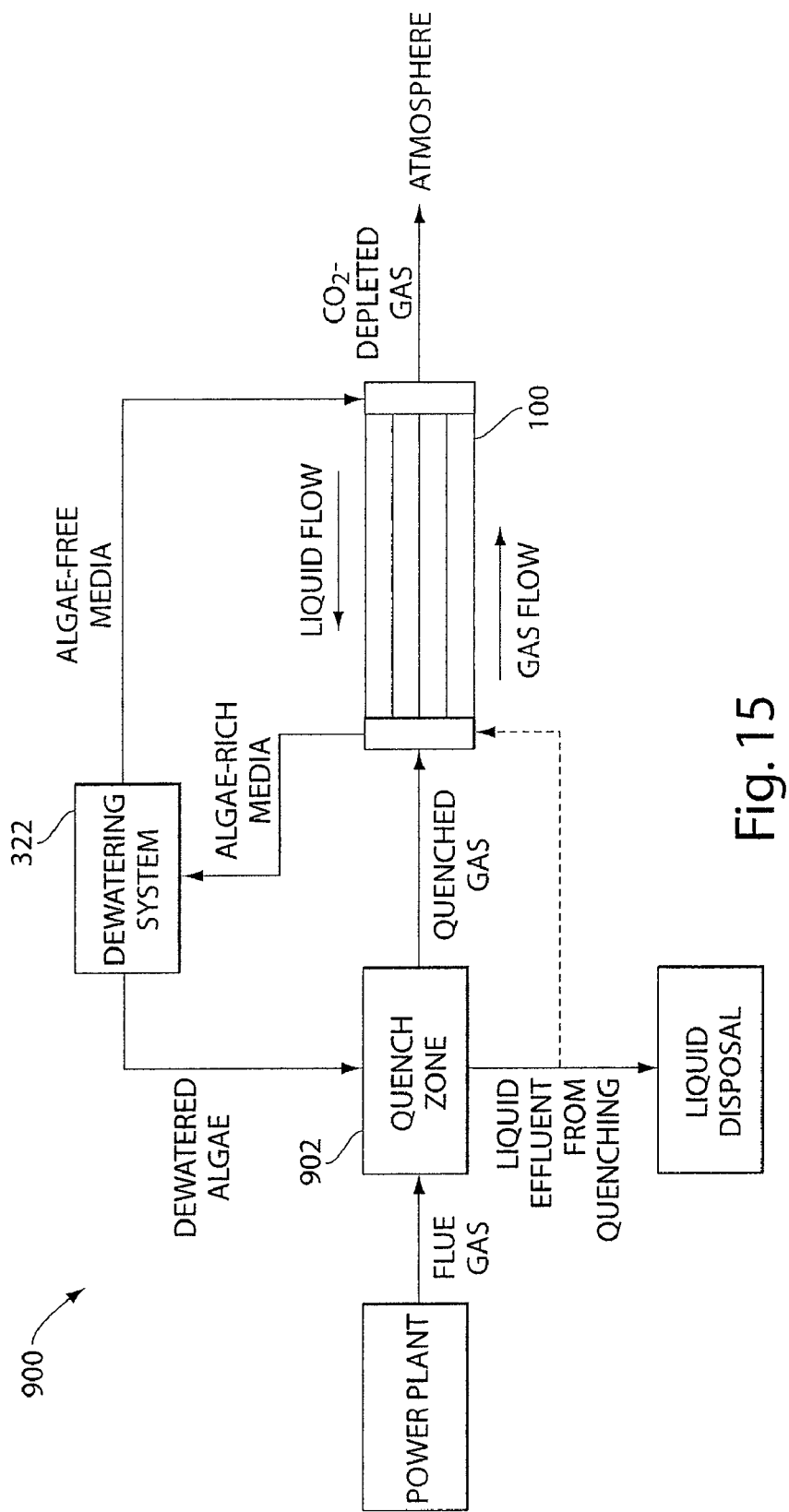
FIG. 15 is a block diagram of an overall gas treatment/biomass production system comprising a photobioreactor system which used liquid associated with the system to quench flue gas.

In a further embodiment of a photobioreactor system including quenching, illustrated in FIG. 15, enriched algae from dewatering system 322 may be used to cool hot flue gas in quench zone 902. Dewatered algae may be approximately 3% solids concentration after primary dewatering, and 10-20% solids after secondary dewatering. Using dewatered algae in quench zone 902 may help to stabilize the algae against decomposition, preheat the algae to aid in downstream processing, and allow some components to react with the acid gases, which may promote downstream processes such as fermentation.

In some embodiments, an integrated system for performing an integrated combustion method may include a photobioreactor system wherein combustion gases are treated with the photobioreactor system to mitigate pollutants and to produce biomass, for example in the form of harvested algae which can be used as a fuel for the combustion device and/or for the production of other products, such as products comprising organic molecules (e.g. fuel grade oil (e.g. biodiesel) and/or organic polymers). Further description of such an integrated system, which can be used in conjunction with embodiments of photobioreactor systems disclosed herein, may be found in commonly-owned PCT Publication No. WO2006/020177 A1, published on Feb. 23, 2006, commonly-owned U.S. Patent Application Publication Nos. US-2005-0064577-A1 and US-2005-0239182-A1, and PCT Application No. US2005/025249, filed on Jul. 18, 2005, each of which is hereby incorporated by reference in its entirety.

Figure 16:
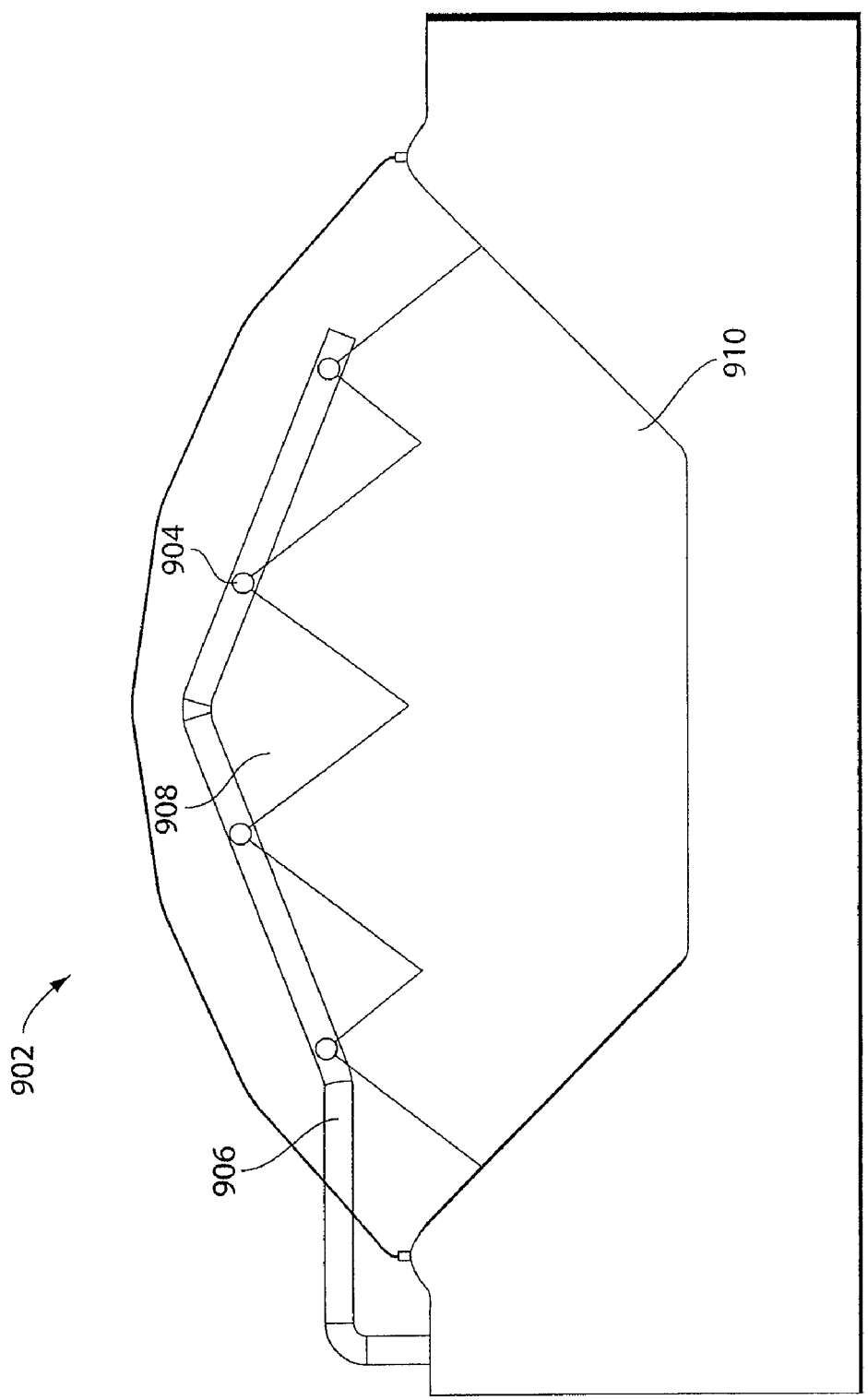
FIG. 16 is a cross-sectional view of a quench zone according to one embodiment of the invention.
Figure 17:
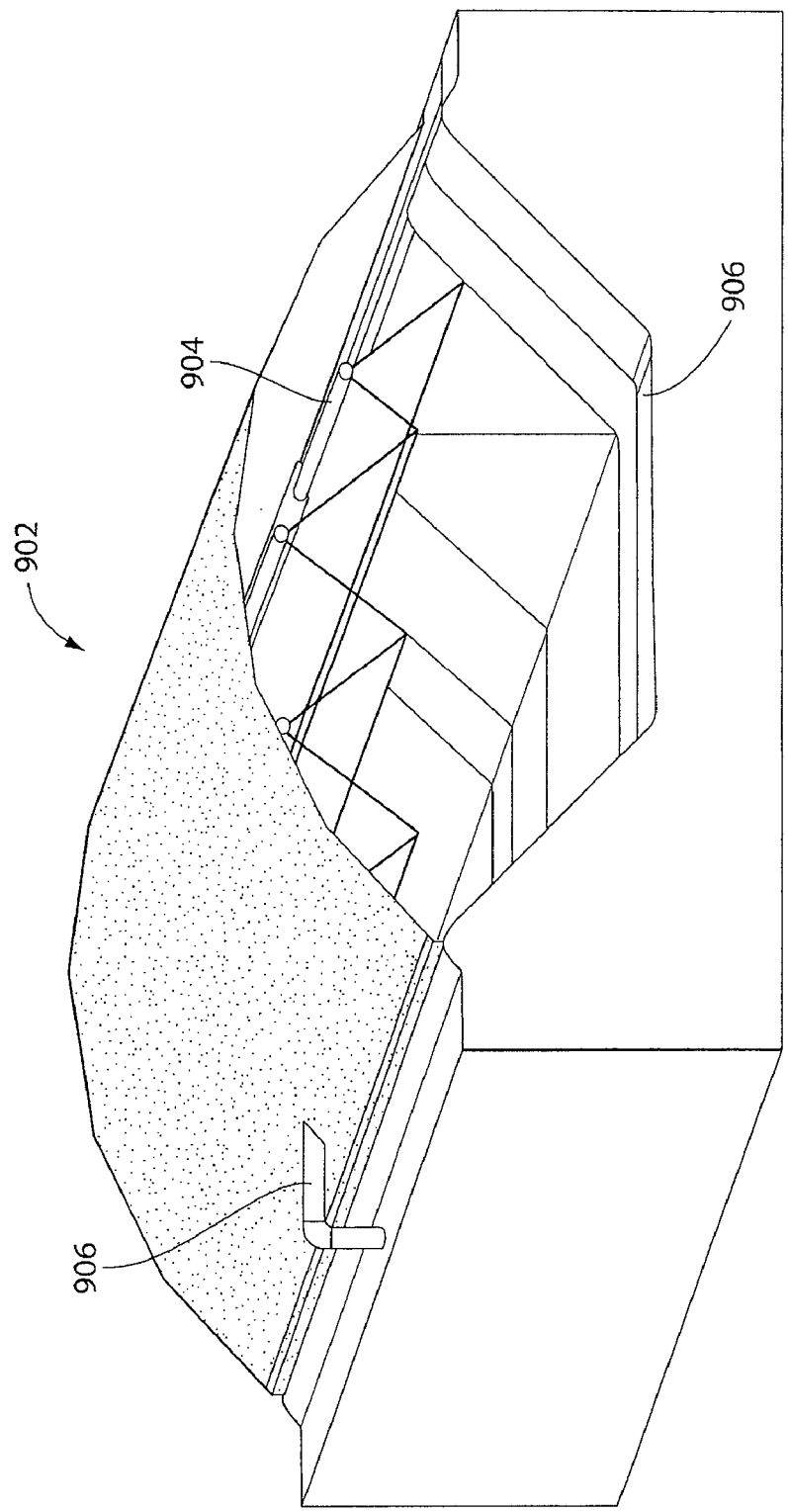
FIG. 17 is a perspective view of the quench zone shown in FIG. 16.

One embodiment of a configuration for quench zone 902 is illustrated in FIG. 16. In this embodiment, spray elements 904 extend perpendicularly to a liquid supply conduit 906 and are configured spray liquid into a gas headspace 908. Liquid effluent is collected from the bottom of a trench 910 and either disposed of or recycled back into the photobioreactor system. A perspective view of one embodiment of quench zone 902 in FIG. 17 illustrates that spray elements 904 may be spray conduits 914 including longitudinal slits.

Figure 18:
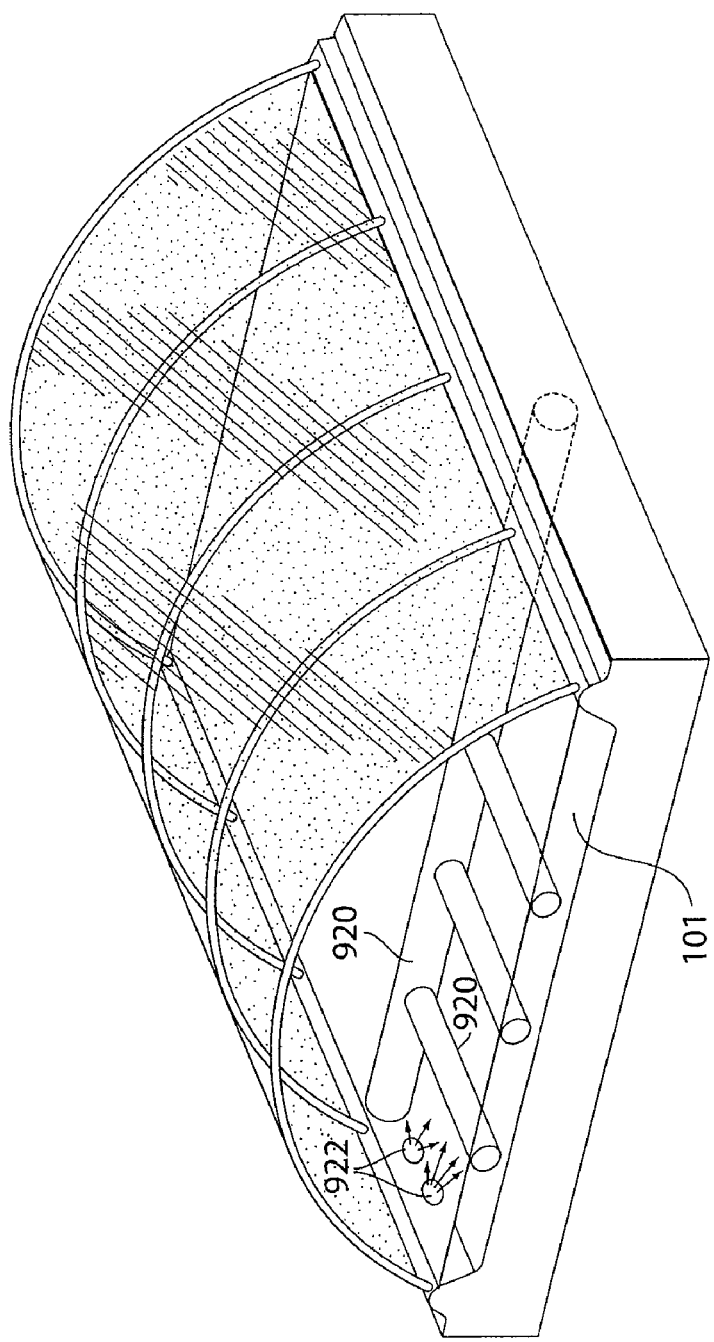
FIG. 18 is a perspective view of a heat exchange zone of a photobioreactor unit according to one embodiment of the invention.

In some embodiments of the invention, waste heat (in the form of heated water) may be used to heat liquid media in a photobioreactor system. One embodiment of tubes 920 submerged in liquid medium 101 is shown in FIG. 18. Tubes 920 in FIG. 18 may continue longitudinally within the same photobioreactor section or unit, and/or may continue laterally to adjacent photobioreactor sections or units. In some embodiments, jets 922 may be used to increase the flow rate of liquid medium 101 past tubes 920 to increase the rate of heat transfer.

PROPHETIC EXAMPLES

Example 1

Figure 19:
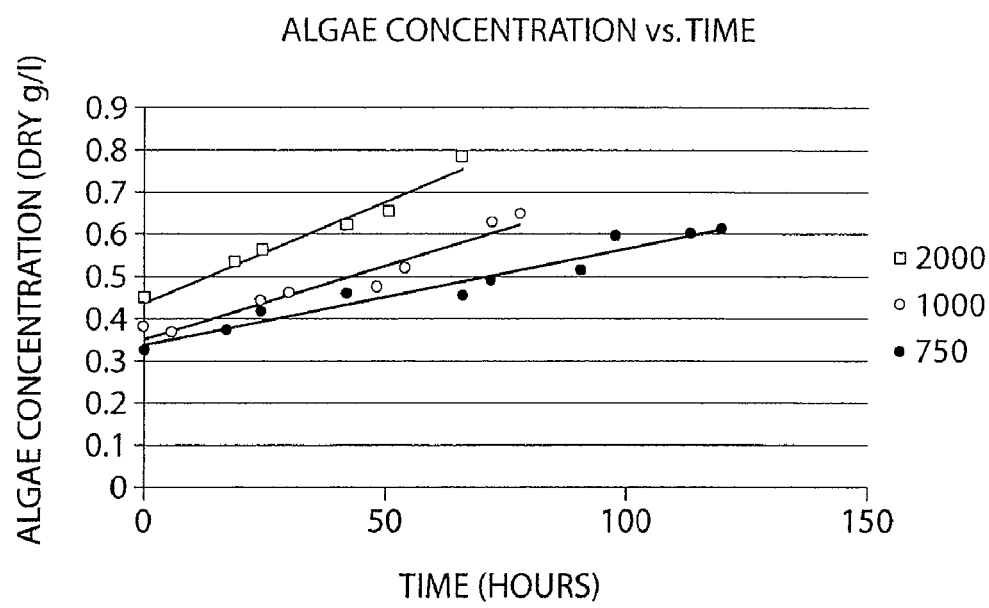
FIG. 19 shows algae concentration versus time for one example of the use of a photobioreactor described herein.

In this example, a laboratory test of an embodiment of a photobioreactor of the present disclosure is compared to a model of the same. Algae species *Nannochloris* sp. is grown in a 20 cm depth of Media 1, which is sea water comprising 0.075 g/l $NaNO_3$ and 0.00565 g/l $NaH_2PO_4.2H_2O$. The growth rates for the algae as a function of time, concentration, and light intensity, measured as photon flux, can be derived from laboratory tests with well-stirred open tanks fed with gas containing 5 mol % $CO_2$ and the balance $O_2$ and $N_2$ in a 1:5 molar ratio. The test results are shown in FIG. 19 for insolation rates of 2000, 1000, and 750 μE/m²·s, and the productivity is tabulated in Table 1. As shown in FIG. 8, the productivity is not a function of concentration in this operating range. Independently, the growth rate can be predicted following the methods of Wu and Merchuk, (A Model Integrating Fluid Dynamics in Photosynthesis and Photoinhibition Processes. Chemical Engineering Science 56:3527-3538, 2001). The parameter $\mu_{max}$ was averaged 0.077 hr-1 in duplicate tests, and parameter kx is taken as 0.22 m2/g per Oswald (*The Engineering Aspect of Microalgae*. In: Laskin, I., and Lechevalier, H. A., Editors. CRC Handbook of Microbiology. Cleveland CRC Press, pp 519-552, 1977.) The model productivities matched the measured productivities well, as shown in Table 1.

Figure 20:
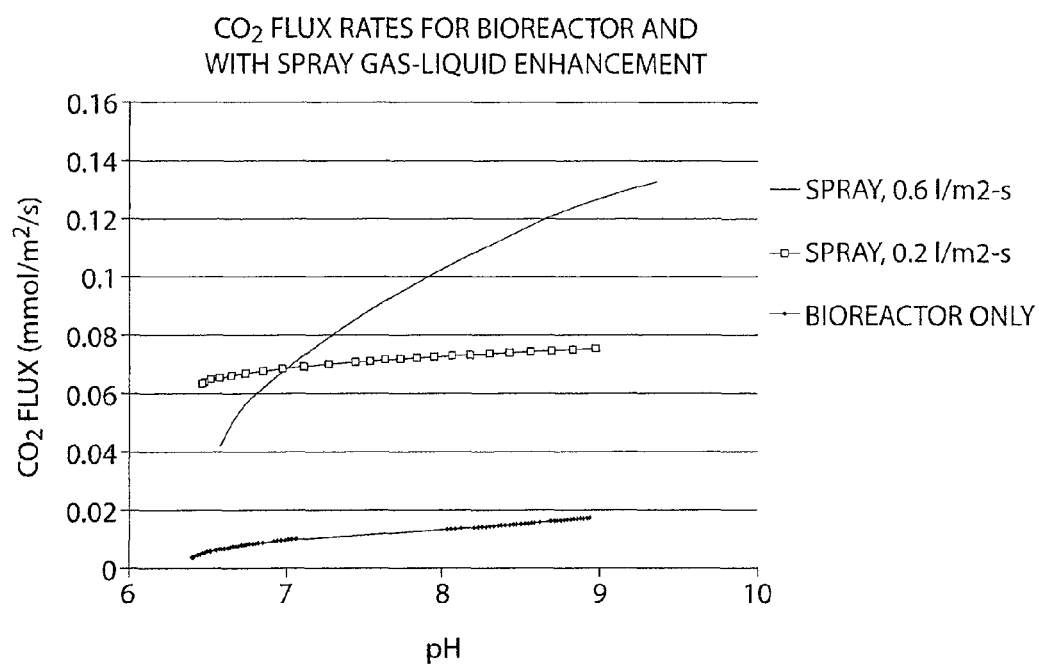
FIG. 20 shows carbon dioxide flux rates for embodiments employing different liquid spray rates.

The bioreactor gas/liquid exchange is measured in a flowing rectangular conduit with 5 mol % $CO_2$ flowing above a media containing base so that $CO_2$ uptake can be measured by carbonate analysis in the liquid phase. The results are shown in FIG. 20, expressed as $CO_2$ flux (mmol/m²-sec) vs pH of the media. Recycled media from dewatering is used to enhance the $CO_2$ gas-liquid exchange. FIG. 20 also show the enhanced gas-liquid mass transfer rates that can be achieved by spraying the recycled media into the headspace of the reactor for two different spray rates, normalized to the reactor area. The test results illustrate the increase in $CO_2$ transfer rates which can be obtained by properly re-injecting the dewatering fluid into the reactor. These higher $CO_2$ transfer rates can reduce the bioreactor area requirements in situations where the algal productivity is limited by gas mass transfer. Alternatively these higher $CO_2$ transfer rates can be used to increase the total biomass production rates from a bioreactor of fixed size.

A covered bioreactor is modeled using the algal growth model discussed above and the mass transfer rates from the gas-liquid tests. The bioreactor has a depth of 20 cm and a liquid velocity of 20 cm/sec to ensure a high level of turbulence. The bioreactor is sufficiently long that the flow is essentially plug flow; i.e. the Peclet number is high. The liquid phase comprises Media 1 maintained at pH 7.8 with an initial algae recycle rate to maintain the algae concentration of in the feed end at 0.1 g cell dry weight/liter. The flue gas contains 5 mol % $CO_2$, and flows through channels with a gas freeboard height of 2 m. The bioreactor is covered with polyethylene plastic film, with a measured visible light transmission of 95%. The media recycled from the dewatering system is split with 80% returned to the bioreactor to enhance the $CO_2$ mass transfer rate, and 20% sent to the open areas of the bioreactor to generate a spray that enhances liquid cooling. The ambient dry-bulb temperature is assumed to be 30° C., with a wet-bulb temperature of 25° C. The reactor productivity, $CO_2$ conversion, power requirements for the flue gas handling and water consumption are listed in Table 2 for three levels of solar insolence. Table 2 also shows

TABLE 2

Comparison of Bioreactor Performance at 30 C. Ambient

| Example | Light Intensity (μE/m2-s) | Reactor productivity (g/m2-hr) | $CO_2$ conversion (mol %) | Power requirement (kW) | Water Consumption (kg/m2-hr) |
|---|---|---|---|---|---|
| Example 1 - Present Embodiment | 2000 | 1.4 | 60% | 1 | 1.1 |
|  | 1000 | 1.1 | 50% | 1 | .5 |
|  | 750 | 0.9 | 40% | 1 | .4 |
| Example 2 - Raceway Pond | 2000 | 1.4 | 20% | 30 | 1.1 |

TABLE 1

Algae Growth Rate

| Light Intensity (μE/m2-s) | Measured Productivity (dry weight g/m2-hr) | Model Predicted Productivity (dry weight g/m2-hr) |
|---|---|---|
| 2000 | 1.4 | 1.4 |
| 1000 | 1.1 | 1.1 |
| 750 | 0.7 | 0.9 |

Example 2

This example illustrates the advantage of embodiments of photobioreactors disclosed herein compared to a conventional raceway pond. The reactor productivity, $CO_2$ conversion, power requirements for the flue gas handling, and water consumption are listed in Table 3 for the highest level of solar insolence using the same operating conditions of Example 1, based on published values for $CO_2$ conversion and evaporation rates. Flue gas is sparged into a 2-meter deep well in the raceway via a blower that compresses flue gas to 8 psig. The results show that the hybrid bioreactor achieves comparable growth rates, while attaining greater $CO_2$ conversion and using substantially less power. The raceway pond power consumption is significantly higher due to its lower $CO_2$ capture efficiency, requiring higher flue gas flows per unit of algae produced, and its higher pressure drop. Water consumption for both reactors is comparable because both use evaporative cooling to maintain reactor temperature.

Example 3

This example illustrates the advantage of the hybrid open/closed bioreactor at a lower ambient temperature, 5° C., compared to a raceway pond. The system of Examples 1 and 2 is operated at identical conditions, with the exception that none of the recycled media of Example 1 is directed towards the cooling zone, and low-level heat from the power plant condenser cooling loop is used to maintain the bioreactor temperature. Table 3 lists the productivity and heat duty for maintaining 25° C. in the two reactors. The results show that this reactor has significant advantages over an open raceway pond.

TABLE 3

Comparison of Bioreactor Performance at 5° C. Ambient

| Example | Light Intensity ($\mu E/m2\text{-}s$) | Reactor productivity (g/m2-hr) | Heat duty (kW/m2) |
|---|---|---|---|
| Example 3 - Photobioreactor | 1000 | 1.1 | 0.02 |
| Example 3 - Raceway pond | 1000 | 1.1 | 0.10 |

Example 4

This example illustrates options for integrating the dewatering operation with the bioreactor. *Nannochloris* sp. is grown in Media 1 at bioreactor temperatures ranging from 17-27 C, with insolation ranging up to about 2200 $\mu E/m2\text{-}s$. The biomass concentration ranges from 0.2 to 10 grams/liter. The algae is dewatered using the techniques known in the art as Dissolved Air Flotation. The feed to the dewatering system is mixed with aluminum sulfate to attain a concentration of 50-300 ppm in the media, and contacted with bubbles generated by dissolving air into the filtrate that is recycled to the dewatering unit at a 10% rate. The algal biomass creates a floe that is 4-5 wt % solids. Essentially algae-free filtrate is recycled to the reactor, allowing unreacted nutrients to be returned to the system. Recycling this stream reduces total water and nutrient requirements. Optionally a portion or all of the dewatering feed stream can be contacted with flue gas in the quench zone prior to dewatering. For flue gases containing acid gases such as $SO_2$, $NO_x$, and HCl, absorption of the acid gases reduces pH from approximately 7-9 range to a more preferred range of 6.5-7.5. In this pH range, the quantity of aluminum sulfate required to dewater the algae is reduced.

Example 5

This example illustrates the use of Tangential Flow Filtration for dewatering the algae. The algae of Example 5 is run in a system using tangential flow filtration instead of dissolved air floatation. The filtration process uses a sterile-grade membrane and operates at low trans-membrane pressure and low shear rates to increase the algae concentration by a factor of 10-200. Cellular debris and bacterial contaminants are concentrated with the algae-rich stream. The sterilized permeate stream is recycled to the reactor, conserving water and nutrients while reducing risk due to recycle of deleterious species such as bacteria and cell lysates.

Example 6

This example illustrates the use of different operating conditions upstream and downstream of the algae recycle point(s) to affect changes in the algae growth rates and algae composition. The bioreactor of Example 1 is operated with the algae recycle zone located ⅔ down the length of the reactor channel. Recycled media is used to add nitrate such that the concentration in the feed end is 0.075 g/l and the concentration in the recycle stream is 0.03 g/l. In the zone downstream of the algae recycle stream split, the recycled media contains nutrients such as phosphate, but no nitrate. The algae in the first zone experience growth rates of 1.4 $g/m^2$-hr, and lipid content is approximately 14 wt %. The algae in the second, nitrate-poor region demonstrate lower growth rates, but have lipids content that exceeds 14 wt %.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. A photobioreactor system comprising:
a plurality of interconnectable photobioreactor sections which, when connected together, form at least one longitudinally-oriented photobioreactor unit of the photobioreactor system, the photobioreactor sections each comprising
a liquid flow channel, and
a light-transparent cover that forms a gas headspace between the cover and the liquid flow channel, the cover being constructed and arranged to cover at least a substantial portion of the liquid flow channel and configured to provide the gas headspace even when a gas pressure within the photobioreactor unit is less than the atmospheric pressure surrounding the photobioreactor section,
at least one photobioreactor unit of the photobioreactor system further including an evaporative cooling area, including a reservoir and a sprayer, the evaporative cooling area being disposed outside of the cover such that the reservoir is open to the atmosphere outside of the cover, the reservoir being in fluid communication with the liquid flow channel, the sprayer_configured to spray a liquid upwardly from within the reservoir.

2. A system as in claim 1, wherein a first subset of the plurality of interconnectable photobioreactor sections comprises a different functionality than a second subset of the plurality of interconnectable photobioreactor sections.

3. A system as in claim 1, wherein the photobioreactor system comprises a plurality of photobioreactor units.

4. A system as in claim 3, wherein the plurality of photobioreactor units are arranged in parallel.

5. A system as in claim 4, wherein the plurality of photobioreactor units each include the same number of sections.

6. A system as in claim 1, wherein the liquid flow channel contain a liquid medium comprising phototrophic organisms.

7. A system as in claim 6, wherein the phototrophic organisms comprise algae.

8. A system as in claim 1, further comprising a gas inlet in fluid communication with the gas headspace, wherein the gas inlet is connected to a source of waste gas having an elevated concentration of $CO_2$.

9. A system as in claim 8, wherein the waste gas comprises a flue gas.

10. A system as in claim 1, further comprising a dewatering system in fluid communication with an output of the at least one longitudinally-oriented photobioreactor unit.

11. A system as in claim 1, further comprising a mister disposed within a photobioreactor section of the plurality of photobioreactor sections and configured to spray a liquid within the gas headspace.

12. A system as in claim 11, wherein the mister is configured to spray the liquid downwardly towards the liquid flow channel.

13. A system as in claim 1, wherein the cover is supported by ribs attached to the base.

14. A system as in claim 1 further comprising two pontoon floats that extend longitudinally along a length of the photobioreactor unit and configured to support the photobioreactor unit on a body of water.

* * * * *